(12) United States Patent
Wu et al.

(10) Patent No.: US 9,873,900 B2
(45) Date of Patent: Jan. 23, 2018

(54) RNA-MEDIATED GENE ASSEMBLY FROM DNA OLIGONUCLEOTIDES

(71) Applicant: Wisconsin Alumni Research Foundation, Madison, WI (US)

(72) Inventors: Cheng-Hsien Wu, Madison, WI (US); Lloyd Smith, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 786 days.

(21) Appl. No.: 13/763,009

(22) Filed: Feb. 8, 2013

(65) Prior Publication Data
US 2013/0225446 A1 Aug. 29, 2013

Related U.S. Application Data

(60) Provisional application No. 61/597,428, filed on Feb. 10, 2012.

(51) Int. Cl.
| | | |
|---|---|---|
| *C12N 15/11* | (2006.01) | |
| *C12P 19/34* | (2006.01) | |
| *C12N 15/10* | (2006.01) | |
| *C12N 15/66* | (2006.01) | |
| *C40B 40/08* | (2006.01) | |
| *C40B 50/06* | (2006.01) | |

(52) U.S. Cl.
CPC ............. *C12P 19/34* (2013.01); *C12N 15/10* (2013.01); *C12N 15/1031* (2013.01); *C12N 15/66* (2013.01); *C40B 40/08* (2013.01); *C40B 50/06* (2013.01)

(58) Field of Classification Search
CPC ...................................................... C12Q 1/68
See application file for complete search history.

(56) References Cited

U.S. PATENT DOCUMENTS

| 2004/0161792 | A1* | 8/2004 | Liao et al. ............... 435/6 |
| 2006/0078889 | A1* | 4/2006 | Bhattacharjee ...... C12Q 1/6837 435/6.11 |
| 2006/0134663 | A1* | 6/2006 | Harkin ................. C12Q 1/6886 435/6.11 |

FOREIGN PATENT DOCUMENTS

| WO | 0017372 | A2 | 3/2000 |
| WO | 0049142 | A1 | 8/2000 |
| WO | 2004024886 | A2 | 3/2004 |
| WO | 2005059096 | A2 | 6/2005 |
| WO | 2010025310 | A2 | 3/2010 |
| WO | 2011085075 | A2 | 7/2011 |

OTHER PUBLICATIONS

Chen et al., Nucleic Acids Research, vol. 18, No. 4, p. 871-78, 1990.*

Jackson et al., TRENDS in Genetics, vol. 20, No. 11, Nov. 2004, p. 524.*
Borovkov, et al., High-Quality Gene Assembly Directly from Unpurified Mixtures of Microarray-Synthesized Oligonucleotides, Nucleic Acids Research, 2010, 38(19):e180, 10 pages.
Cleary, et al., Production of Complex Nucleic Acid Libraries Using Highly Parallel In Situ Oligonucleotide Synthesis, Nature Methods, 2004, 1(3):241-248.
Crippa, et al., Characterisation of Adducts of Nucleic Bases and Acrylic Monomers, Gazzetta Chimica Italiana, 1993, 123(4):197-203.
Gao, et al., Methylation of Thymine Residues During Oligonucleotide Synthesis, Nucleic Acids Research, 1985, 13 (2):573-584.
Guo, et al., Direct Fluorescence Analysis of Genetic Polymorphisms by Hybridization with Oligonucleotide Arrays on Glass Supports, Nucleic Acids Research, 1994, 22(24):5456-5465.
Hochuli, et al., Genetic Approach to Facilitate Purification of Recombinant Proteins with a Novel Metal Chelate Adsorbent, Nature Biotechnology, 1988, 6:1321-1325.
Itakura, et al., Expression in *Escherichia coli* of a Chemically Synthesized Gene for the Hormone Somatostatin, Science, 1977, 198(4321):1056-1063.
Kim, et al., Progress in Gene Assembly from a MAS-Driven DNA Microarray, Microelectronic Engineering, 2006, 83 (4-9):1613-1616.
Kozak, An Analysis of 5'-Noncoding Sequences from 699 Vertebrate Messenger RNAs, Nucleic Acids Research, 1987, 15(20):8125-8148.
Lockett, et al., Carbon-on-Metal Films for Surface Plasmon Resonance Detection of DNA Arrays, J. Am. Chem. Soc., 2008, 130(27):8611-8613.
Lockett, et al., Fabrication and Characterization of DNA Arrays Prepared on Carbon-on-Metal Substrates, Anal. Chem., 2009, 81(15):6429-6437.
Martin, et al., Processivity in Early Stages of Transcription by T7 RNA Polymerase, Biochemistry, 1988, 27:3966-3974.
McGall, et al., The Efficiency of Light-Directed Synthesis of DNA Arrays on Glass Substrates, J. Am. Chem. Soc., 1997, 119(22):5081-5090.
Milligan, et al., Oligoribonucleotide Synthesis Using T7 RNA Polymerase and Synthetic DNA Templates, Nucleic Acids Research, 1987, 15(21):8783-8798.
Milligan, et al., Synthesis of Small RNAs Using T7 RNA Polymerase, Methods in Enzymology, 1989, 180:51-62.
Nilsson, et al., Chemical Synthesis of Proteins, Annu. Rev. Biophys. Biomol. Struct., 2005, 34:91-118.
Pease, et al., Light-Generated Oligonucleotide Arrays for Rapid DNA Sequence Analysis, Proc. Natl. Acad. Sci. USA, 1994, 91:5022-5026.
Phillips, et al., In Situ Oligonucleotide Synthesis on Carbon Materials: Stable Substrates for Microarray Fabrication, Nucleic Acids Research, 2008, 36(1):e7, 9 pages.

(Continued)

*Primary Examiner* — Celine Qian
(74) *Attorney, Agent, or Firm* — Boyle Fredrickson S.C.

(57) ABSTRACT

The present invention is directed to methods and materials for RNA-mediated gene assembly from oligonucleotide sequences. In some embodiments, the oligonucleotides used for gene assembly are provided in an array format. An RNA polymerase promoter is appended to surface-bound oligonucleotides and a plurality of RNA copies of each oligonucleotide are then produced with an RNA polymerase. These RNA molecules self-assemble into a desired full-length RNA transcript by hybridization and ligation. The resulting RNA transcript may then be converted into double strand DNA useful in a variety of applications including protein expression.

6 Claims, 26 Drawing Sheets

(56) References Cited

OTHER PUBLICATIONS

Pon, et al., Modification of Guanine Bases by Nucleoside Phosphoramidite Reagents During the Solid Phase Synthesis of Oligonucleotides, Nucleic Acids Research, 1985, 13(18):6447-6465.
Pon, et al., Prevention of Guanine Modification and Chain Cleavage During the Solid Phase Synthesis of Oligonucleotides Using Phosphoramidite Derivatives, Nucleic Acids Research, 1986, 14(16):6453-6470.
Prime, et al., Adsorption of Proteins Onto Surfaces Containing End-Attached Oligo(ethylene oxide): A Model System Using Self-Assembled Monolayers, J. Am. Chem. Soc., 1993, 115:10714-10721.
Quan, et al., Parallel On-Chip Gene Synthesis and Application to Optimization of Protein Expression, Nature Biotechnology, 2011, 29:449-452.
Singh-Gasson, et al., Maskless Fabrication of Light-Directed Oligonucleotide Microarrays Using a Digital Micromirror Array, Nature Biotechnology, 1999, 17:974-978.
Stemmer, et al., Single-Step Assembly of a Gene and Entire Plasmid From Large Numbers of Oligodeoxyribonucleotides, Gene, 1995, 164:49-53.
Tian et al., Accurate Multiplex Gene Synthesis From Programmable DNA Microchips, Nature, 2004, 432:1050-1054.
Walbert, et al., Photolabile Protecting Groups for Nucleosides: Mechanistic Studies of the 2-(2-Nitrophenyl)ethyl Group, Helvetica Chimica Acta, 2001, 84(6):1601-1611.
Xiong, et al., A Simple, Rapid, High Fidelity and Cost-Effective PCR-Based Two-Step DNA Synthesis Method for Long Gene Sequences, Nucleic Acids Research, 2004, 32(12):e98, 10 pages.
Kosuri, et al., Scalable Gene Synthesis by Selective Amplification of DNA Pools from High-Fidelity Microchips, Nature Biotechnology, 2010, 28(12):1295-1299.
Matzas, et al., High-Fidelity Gene Synthesis by Retrieval of Sequence-Verified DNA Identified Using High-Throughput Pyrosequencing, Nature Biotechnology, 2010, 28(12):1291-1294.
Richmond, et al., Amplification and Assembly of Chip-Eluted DNA (AACED): A Method for High-Throughput Gene Synthesis, Nucleic Acids Research, 2004, 32(17):5011-5018.
Wu, et al., RNA-Mediated Gene Assembly from DNA Arrays, Angew. Chem. Int. Ed., 2012, 51:4628-4632.
Wu, et al., Supporting Information: RNA-Mediated Gene Assembly from DNA Arrays, Angew. Chem. Int. Ed., 2012, vol. 51, pp. 1-19.
Xiong, et al., Non-Polymerase-Cycling-Assembly-Based Chemical Gene Synthesis: Strategies, Methods, and Progress, Biotechnology Advances, 2008, 26:121-134.
PCT International Search Report and Written Opinion, PCT/US2013/025343, dated May 14, 2013.

* cited by examiner

```
                      710
                 ....|....|....
ZsGreen1         ACCATCACCACTAG
01A_1.ab1        ..............
01B_2.ab1        ..............
01C_3.ab1        ..............
01D_4.ab1        ..............
01E_5.ab1        ..............
01F_6.ab1        ..............
01G_7.ab1        ..............
01H_8.ab1        ..............
02A_9.ab1        ..............
02B_10.ab1       ..............
02C_11.ab1       ..............
02D_12.ab1       ..............
02E_13.ab1       ..............
02F_14.ab1       ..............
02G_15.ab1       ..............
02H_16.ab1       ..............
03A_17.ab1       ..............
03B_18.ab1       ..............
03C_19.ab1       ..............
03D_20.ab1       ..............
03E_21.ab1       ..............
03F_22.ab1       ..............
03G_23.ab1       ..............
03H_24.ab1       ..............
04A_25.ab1       ..............
```

```
                           710
                  ....|....|....|..
ZsGreen1          CACCA TCACCAC TAC
04B_26.ab1        ..... ....... ...
04C_27.ab1        .....A ....... ...
04D_28.ab1        ..... ....... ...
04E_29.ab1        ..... ....... ...
04F_30.ab1        ..... ....... ...
04G_31.ab1        ..... ....... ...
04H_32.ab1        ..... ....... ...
05A_33.ab1        ..... ......T ...
05B_34.ab1        ..... ....... ...
05C_35.ab1        ..... ....... ...
05D_36.ab1        ..... ....... ...
05E_37.ab1        ..... ....... ...
05F_38.ab1        ..... ....... ...
05G_39.ab1        ..... ....... ...
05H_40.ab1        ..... ....... ...
06A_41.ab1        ..... ....... ...
06B_42.ab1        ..... ....... ...
06C_43.ab1        ..... ....... ...
06D_44.ab1        ..... ....... ...
06E_45.ab1        ..... ....... ...
06F_46.ab1        ..... ....... ...
06G_47.ab1        ..... ....... ...
06H_48.ab1        ..... ....... ...
07A_49.ab1        ..... ....... ...
07B_50.ab1        ..... ....... ...
07C_51.ab1        ..... ....... ...
```

RNA-MEDIATED GENE ASSEMBLY FROM DNA OLIGONUCLEOTIDES

CROSS-REFERENCE TO RELATED APPLICATION

This application claims priority to U.S. Provisional Patent Application No. 61/597,428 filed on Feb. 10, 2012, and incorporated by reference herein in its entirety.

STATEMENT REGARDING FEDERALLY SPONSORED RESEARCH OR DEVELOPMENT

This invention was made with government support under HG004952 awarded by the National Institutes of Health. The government has certain rights in the invention.

FIELD OF THE INVENTION

The present invention relates to methods and materials for RNA-mediated gene assembly from oligonucleotide sequences on a DNA array. More particularly, an RNA polymerase promoter is appended to surface-bound oligonucleotides, RNA copies are produced using an RNA polymerase, the RNA copies undergo self-assembly and are subsequently ligated to provide a full-length target RNA molecule. The RNA molecule is readily copied by RT-PCR to yield the corresponding gene or target double strand DNA fragment.

BACKGROUND OF THE INVENTION

The widespread availability of peptides and oligonucleotides synthesized by solid-phase chemistries has had a profound impact upon biology and medicine, with myriad important uses in research, diagnostics, and therapeutics. A limitation of current technologies is the relatively short length of the molecules that can be synthesized, as determined by the stepwise reaction yield, and thus peptides and oligonucleotides are usually restricted to lengths below ~50 amino acids or ~100 nucleotides (nt), respectively. This synthetic limitation has driven interest in the development of alternative approaches for the production of full-length genes and proteins. The most common strategy has been to splice together shorter segments into a full-length, functional assembly; for example, the Staudinger ligation reaction permits full-length proteins to be constructed from a series of peptides (1), and full-length genes can be obtained from multiple short single strands in a series of sequential ligation steps (2) or by Polymerase Cycling Assembly (PCA) (3). However, the assembly-based strategies for gene synthesis reported to date remain laborious, expensive, and time-consuming, and thus have not yet provided the level of accessibility needed for widespread utility. As can be appreciated from the above discussion, a need exists for improved methods and materials that reduce the labor, expense and time involved in assembly-based gene synthesis.

SUMMARY OF THE INVENTION

The present invention is based on the inventor's recent discovery of an RNA-mediated assembly method using oligonucleotide sequences on a DNA array. The inventors' strategy facilitates assembly of full-length RNA transcripts useful in a variety of life science applications, including gene synthesis and protein expression.

Accordingly, in a first aspect described herein is a method for RNA-mediated assembly method for providing a target RNA molecule. Such a method includes steps of: (a) providing an oligonucleotide array comprised of: (i) a plurality of first oligonucleotides each having a segment sequence corresponding to a portion of a target RNA and a complementary RNA Polymerase (RNAP) promoter sequence operably-linked to the segment sequence's 3' termini; and (ii) a plurality of second oligonucleotides each having a splint sequence corresponding to a portion of the target RNA that complements and partially overlaps the segment sequence of the first oligonucleotides, the second oligonucleotides including a RNAP promoter sequence operably-linked to their splint sequence's 3' termini; (b) hybridizing a third oligonucleotide encoding a RNAP promoter sequence to the complementary RNAP promoter sequence of the first and second pluralities of oligonucleotides to yield double-stranded RNAP promoters; (c) transcribing with RNA polymerase, in the presence of rNTPs, the segment sequence of the first plurality of oligonucleotides to yield an RNA segment and the splint sequence of the second plurality of oligonucleotides to yield an RNA splint; (d) assembly of the RNA segments and RNA splints by hybridization to form RNA:RNA hybrids; and (e) sealing nicks in the RNA:RNA hybrid to provide a target RNA molecule.

In some embodiments, sealing of nicks in the RNA:RNA hybrid is carried out using any nucleic acid modifying enzyme suitable for ligation of RNA, such as T4 RNA ligase 2 (or a truncated version). In other embodiments where 2'-O-Methyl ribonucleotides are used for RNA splint preparation, sealing of nicks in the RNA:RNA hybrid is carried out using any nucleic acid modifying enzyme suitable for ligation of RNA with a DNA splint, such as T4 DNA ligase or a truncated version thereof.

In some embodiments, the plurality of first oligonucleotides or the plurality of second oligonucleotides is provided as a surface-bound oligonucleotide array.

In certain embodiments, in step (c), transcription is carried out in the presence of a mixture of rNTPs and rNMPs.

In other embodiments, the method includes removal of any terminal pyrophosphates from the RNA segments and RNA splints is carried out using any nucleic acid modifying enzyme suitable for removing such phosphate moieties, such as 5' pyrophosphohydrolase or RNA pyrophosphatase.

In certain embodiments, the complementary RNAP promoter sequence operably-linked to the segment sequence and the splint sequence is a complementary T7 RNAP promoter sequence or a complementary T3 RNAP promoter sequence.

In some embodiments of the method, the 5' end of each segment sequence and each splint sequence corresponds to a GG dinucleotide in the target RNA molecule.

The inventive method advantageously allows that steps (d)-(f) in the above-described method may be, at the discretion of the operator, carried out successively without intervening buffer exchange. Such option reduces costs associated with operator labor and time, and costs of reagents and related laboratory materials.

In preferred methods of the invention, the RNA-mediated assembly method is based on a target RNA molecule that is a full-length RNA transcript of a gene.

In some embodiments, methods utilize surface-bound oligonucleotides which include a spacer, a T7 RNAP promoter sequence, a CC dinucleotide and either the segment sequence or the splint sequence.

In some embodiments, where the method utilizes surface-bound oligonucleotides, the surface-bound oligonucleotides include a 3' (dT)$_{10}$ spacer, a CTG trinucleotide, a 17mer T7 RNAP promoter sequence, a CC dinucleotide and either the segment sequence or the splint sequence. In other embodiments, a polyethylene glycol (e.g., PEG-2000) is used as the spacer.

The RNAP promoter sequence contained in the third oligonucleotide is in some cases a T7 RNAP promoter sequence or a T3 RNAP promoter sequence In some embodiments, the third oligonucleotide includes a T7 RNAP promoter sequence and a dinucleotide GG, and in other embodiments comprises a trinucleotide CTG, a 17 mer T7 RNAP promoter sequence and a dinucleotide GG, AG, or a single nucleotide.

In a second and related aspect, the invention provides an RNA-mediated gene assembly method for providing a target gene. Such a method includes steps of: (a) reverse-transcribing an RNA target molecule provided by any one of the inventive methods described herein; (b) purifying the target gene.

In a third and related aspect, the invention provides an RNA-mediated method for providing a target protein. Such a method includes steps of: (a) reverse transcribing an RNA target molecule provided by any one of the inventive methods described herein to provide a target gene; (b) expressing a target protein encoded by the target gene; and (c) purifying the target protein.

In another aspect, the invention encompasses an oligonucleotide array for RNA-mediated assembly of a target RNA molecule. Such an array includes: (a) a plurality of first surface-bound oligonucleotides each having a segment sequence corresponding to a portion of a target RNA and a complementary RNAP promoter sequence operably-linked to the segment sequence's 3' termini; and (b) a plurality of second surface-bound oligonucleotides each having a splint sequence corresponding to a portion of the target RNA that complements and partially overlaps the segment sequence of the first surface-bound oligonucleotides, the second surface-bound oligonucleotides including a RNAP promoter sequence operably-linked to their splint sequence's 3' termini, wherein the first and second surface-bound oligonucleotides are linked at their 3' termini to a surface of the oligonucleotide array.

In preferred embodiments, the target RNA molecule is a full-length RNA transcript of a gene.

As noted above, a variety of standard and readily obtainable components and reagents may be utilized in the combination of inventive steps. For example, the oligonucleotide array's surface may be silanized glass or, alternatively, amorphous carbon deposited on a gold film. Accordingly, oligonucleotide arrays useful in the present methods may be provided by any standard fabrication process known in the field including, but not limited to, in situ photolithographic oligonucleotide array synthesis.

In certain embodiments, the complementary RNAP promoter sequence operably-linked to the segment sequence and the splint sequence is a complementary T7 RNAP promoter sequence or a complementary T3 RNAP promoter sequence.

In some embodiments, arrays include surface-bound oligonucleotides which have a spacer, a 17mer T7 RNAP promoter sequence, a CC dinucleotide and either the segment sequence or the splint sequence. In some embodiments, arrays include surface-bound oligonucleotides which have a 3' (dT)$_{10}$ spacer, a CTG trinucleotide, a 17mer T7 RNAP promoter sequence, a CC dinucleotide and either the segment sequence or the splint sequence. Alternatively, the surface-bound oligonucleotides include a PEG-2000 instead of (dT)$_{10}$ as the spacer.

In certain embodiments, the array includes a third oligonucleotide which has an RNAP promoter sequence complementary to the RNAP promoter sequence of the first and second surface-bound oligonucleotides and which hybridizes with those surface-bound oligonucleotides to yield double-stranded RNAP promoters. In some embodiments, the third oligonucleotide is a T7 RNAP promoter sequence or a T3 RNAP promoter sequence, more preferably the third oligonucleotide includes a T7 RNAP promoter sequence and a dinucleotide GG, AG, or even a single A. In some embodiments comprising arrays, the third oligonucleotide includes a trinucleotide CTG, a 17 mer and a T7 RNAP promoter sequence.

In some embodiments, the first surface-bound oligonucleotides and/or the second surface-bound oligonucleotides are bound to the surface of a plurality of beads.

As can be appreciated, the invention encompasses the use of oligonucleotide arrays as described herein for use in RNA-mediated assembly of a target RNA molecule. This invention provides the advantage over prior technologies in that embodiments of the invention include fewer manipulation steps and require less operator time than prior technologies.

In yet another aspect, the present invention is useful for the preparation of multiple copies of target RNA molecules, including RNA pools/libraries. Such oligonucleotide array-based methods to provide target RNA molecules include steps of: (a) providing an oligonucleotide array comprised by a plurality of surface-bound oligonucleotides each having a segment sequence corresponding to a portion of a target RNA and a complementary RNAP promoter sequence operably-linked to the segment sequence's 3' termini; (b) hybridizing an oligonucleotide encoding a RNAP promoter sequence to the complementary RNAP promoter sequence of the surface-bound oligonucleotides to yield double-stranded RNAP promoters; and (c) transcribing the segment sequence of the surface-bound oligonucleotide that corresponds to the portion of the target RNA sequence with RNA polymerase to yield multiple copies of a target RNA molecule. In preferred embodiments, a pool of target RNA molecules differing in nucleotide sequences is provided by the method.

In a related aspect, the invention provides oligonucleotide arrays useful for carrying out the methods described in the preceding paragraph. Such oligonucleotide arrays include a plurality of surface-bound oligonucleotides each having a segment sequence corresponding to a portion of a target RNA and a complementary RNAP promoter sequence operably-linked to said segment sequence's 3' termini. In certain embodiments, the arrays further include an oligonucleotide encoding a RNAP promoter sequence hybridized to the complementary RNAP promoter sequence of the surface-bound oligonucleotides to yield double-stranded RNAP promoters.

In a further aspect, the invention provides an oligonucleotide library for RNA-mediated assembly of a target RNA molecule, where the library includes (a) a plurality of first oligonucleotides each having a segment sequence corresponding to a portion of a target RNA and a complementary RNAP promoter sequence operably linked to the segment sequences' 3' termini; and (b) a plurality of second oligonucleotides each having a splint sequence corresponding to a portion of the target RNA that complements and partially overlaps the segment sequence of the plurality of first oligonucleotides, where the second plurality of oligonucleotides includes an RNAP promoter sequence operably linked to their splint sequences' 3' termini.

Other objects, features and advantages of the present invention will become apparent after review of the specification, claims and drawings. The detailed description and examples enhance the understanding of the invention, but are not intended to limit the scope of the appended claims.

INCORPORATION BY REFERENCE

All publications, patents, and patent applications mentioned in this specification are herein incorporated by reference to the same extent as if each individual publication, patent, and patent application was specifically and individually indicated to be incorporated by reference.

DETAILED DESCRIPTION OF THE INVENTION

I. In General

Figure 1:
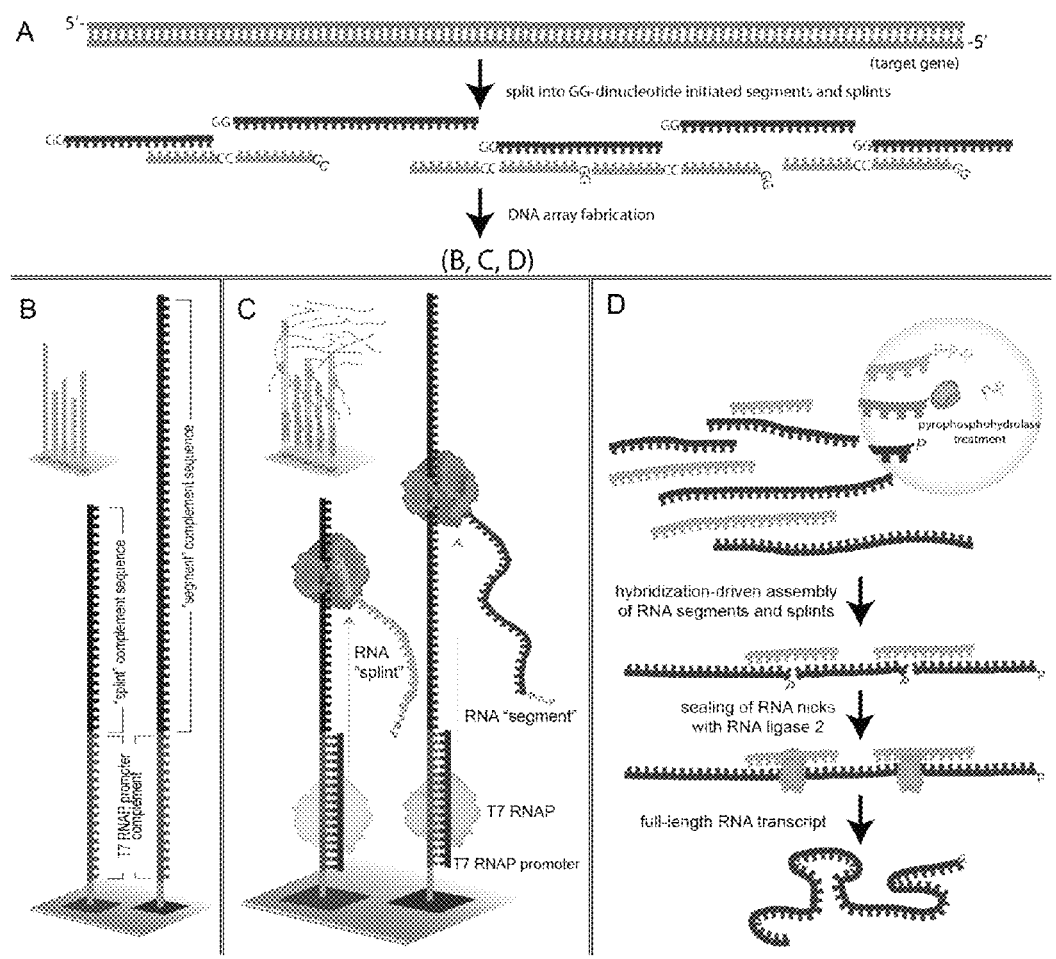
FIG. 1 is an illustration of the RNA-mediated gene assembly process. A) design of segment (red) and splint (blue) sequences to be employed. B) Segment (dark red) and splint (dark blue) complement sequences as synthesized on the DNA array with the complement of the T7 RNAP promoter sequence (green) at their 3' termini. C) Hybridization of an oligonucleotide encoding the T7 promoter sequence yields the necessary double-stranded promoter, and addition of RNA polymerase causes transcription to occur. D) RNA segments and splints have their terminal pyrophosphates removed, assemble by DNA hybridization, and nicks are sealed to yield the desired full-length RNA.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The practice of the present invention will employ, unless otherwise indicated, conventional techniques of medicinal chemistry, pharmacology, organic chemistry, analytical chemistry, molecular biology, microbiology, and immunology, which are within the skill of the art. Such techniques are explained fully in the literature.

Gene assembly from DNA arrays was first described in 2004 (4), and has since been the subject of several other reports (5-10). Its allure lies in the potential to make complete genes as rapidly and inexpensively as single oligonucleotides are made today, enabled by the ability of DNA arrays to easily provide many thousands of oligonucleotides for assembly. However, gene assembly has remained a costly and laborious endeavor. Reasons for this include: (a) the oligonucleotides that are synthesized on DNA arrays must be cleaved from the surface prior to use, and are impure, containing many truncated or chemically modified sequences and thus necessitating various labor- and time-intensive purification or error correction procedures (4,6-10); (b) only minute amounts of oligonucleotide are made per array feature, necessitating complicated amplification strategies that include adaptor ligation and several other steps (4,6-10); (c) virtually all strategies reported to date are based upon Polymerase Cycling Assembly (PCA) (4-11), which although widely used, is complex, laborious, and prone to error (12).

We will now describe an improved method of assembly of full-length RNA transcripts from DNA array by reference to an exemplary embodiment. Referring to FIG. 1, which illustrates one embodiment of the invention, each element of the DNA array includes a T7 RNA polymerase promoter sequence at the 5' end. Transcription from these surface-bound promoters yields many RNA copies of the oligonucleotide elements encoded in the array. These amplified RNA molecules self-assemble to yield the desired full-length transcript. The transcript, once synthesized, is readily copied by RT-PCR to yield the corresponding gene.

To provide proof-of-principle, we designed an oligonucleotide array with the sequences necessary to produce a full-length transcript for the fluorescent protein ZsGreen1. We chose ZsGreen1 for a proof-of-principle demonstration for several reasons: (a) the protein is relatively small in size, consisting of 231 amino acids; (b) has been shown to fold correctly under in vitro translation conditions; and (c) is fluorescent and thus its translation is easily monitored. A full-length RNA transcript, comprising the 696 nt that encode ZsGreen1 and an additional 10 nt corresponding to the Kozak consensus sequence (5'-GGT CGC CAC C-3' (SEQ ID NO:79), added to the 5' end of the RNA transcript to enhance eukaryotic in vitro translation efficiency (13)), was assembled from RNAs produced from photolithographically fabricated oligonucleotide arrays. The 706 nt RNA molecule was divided into 18 segment sequences and 17 splints, ranging in length from 18 to 58 nt.

FIG. 1 depicts one embodiment of the process of generating RNA sequences from a DNA microarray followed by their assembly and ligation to produce the desired full-length RNA molecule. In this embodiment, the process consists of six successive steps, as follows: (a) design the oligonucleotide array; (b) fabricate the array; (c) produce many RNA copies of each array element ("splints" and "segments", see FIG. 1 and the text below) using T7 RNA polymerase; (d) remove 5' terminal pyrophosphates on the splints and segments with RNA 5' pyrophosphohydrolase; (e) allow self-assembly of the splints and segments into the desired full-length construct by RNA:RNA hybridization; and (f) seal the nicks with T4 RNA ligase 2. This final RNA product may then be converted into a DNA copy by reverse transcription, whereupon it may be either cloned, or employed directly to produce more full-length RNAs for in vitro translation or other purposes.

Oligonucleotide arrays were designed to encode "segment sequences" which are the sections of the desired full-length RNA transcript, and "splint sequences" which are complementary RNAs that serve as templates to direct the correct assembly of the RNA segments (FIG. 1A). Two parameters determined the choice of segment and splint composition in the exemplary embodiment: first, each was at least about 30 nucleotides (nt) in length, in order to provide at least two 15 nt stretches of sequence for hybridization during assembly. Second, it was required that the 5' end of each RNA transcript corresponded to a GG dinucleotide, based upon the higher efficiency of transcription exhibited by T7 RNA polymerase when multiple guanine nucleotides are present at the 5' terminus of the transcript being synthesized (see FIG. 1A) (14). GGG trinucleotide sequences at the 5' terminus were avoided however, as they have been shown to give rise to a ladder of poly G transcripts in which the number of G residues can range from 1-3 G, attributed to "slippage" of the enzyme during coupling of GTP (15).

It should be noted that, in general design terms, splint and segment sequences may be shorter or longer than the particular sequences described for the exemplary example, and individual segment sequences may share less than or more than 15 nucleotides for hybridization with their respective splints sequences. It is preferred that the overlap between splint and segment sequences should be designed to share an overlap of about 15 nucleotides on a melting temperature (Tm) normalized basis in order to ensure adequate hybridization between respective splint and segment sequences.

Figure 2:
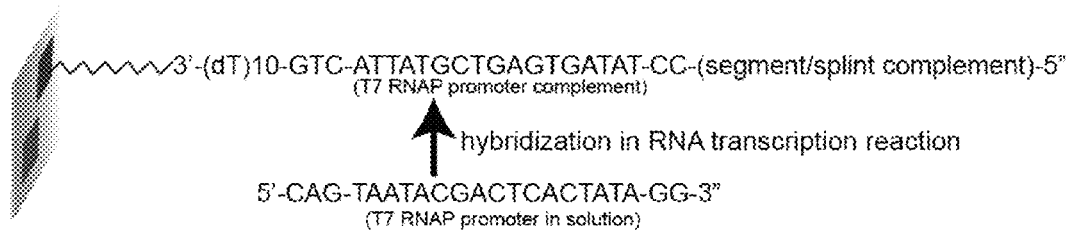
FIG. 2 shows design details of the surface-bound oligonucleotides (the T7 RNAP promoter complement sequence shown at the top of FIG. 2 is SEQ ID NO:80), along with their complements from solution (the T7 RNAP promoter sequence in solution shown at the bottom of FIG. 2 is SEQ ID NO:81).

The design criteria in the exemplary embodiment yielded 18 segment sequences to encompass the desired 706 nt transcript. Each of the 17 splint sequences had a length of 32 nt, corresponding to two 15 nt regions complementary to the segments that it was to join, and an additional 5' GG dinucleotide to enhance transcription efficiency. Each surface-bound oligonucleotide also included at the 3' end a 10 base dT spacer sequence (16), and the three base sequence CTG to improve the hybridization stability of the T7 RNA polymerase complement (see below). The overall design of the surface-bound oligonucleotides is illustrated in FIG. 2, and thus consists of five different sequences; a 3' (dT)10 spacer, a CTG trinucleotide, the 17mer T7 promoter sequence, a CC dinucleotide, and finally the desired segment or splint sequence. In order to make the necessary double-stranded T7 RNA polymerase promoter, the 22 nt complement (consisting of the three nt CTG complement, the 17 nt T7 promoter complement, and the 2 nt GG complement) is included in the T7 RNA transcription reaction. The addition of RNA polymerase results in the synthesis of multiple copies of each RNA segment from each oligonucleotide sequence (FIG. 1B).

The DNA arrays used here were in situ synthesized, in a base-by-base manner, using maskless array synthesizer (MAS) technology (17,18). The arrays were synthesized on either glass or amorphous carbon substrates with similar results: silanized glass substrates are the industry standard for DNA microarrays, whereas we have found that DNA arrays fabricated on amorphous carbon substrates are more stable than their glass analogs to prolonged incubations at elevated temperatures and repeated hybridization cycles (19,20).

The fidelity of the oligonucleotide sequences on the microarray is important for the correct assembly of a full-length RNA transcript. The light-directed synthesis protocols used in this work were thoroughly optimized to maximize sequence fidelity and to reduce the number of errors that occur during array fabrication. Synthesis errors—which can result in truncates, incorrect sequences, etc.—are not detrimental to hybridization-based assays, but can have adverse consequences in the production of useful gene and protein products. The Examples section below describes the protocols employed in the present work, and highlights the differences from previously published protocols (18,20).

Milligan et al. have shown that T7 RNA polymerase will produce RNAs from single-stranded synthetic DNA templates having a duplex DNA promoter, producing hundreds to thousands of RNA transcripts per template molecule (14,21). This amplification capability is central to the approach described here, as the increased concentrations of segment and splint strands drive the hybridization-based assembly process, obviating the need for further PCR amplification prior to the polymerase cycling assembly (PCA) employed in all other gene assembly strategies reported to date (4,6,7,9-11).

The assembly of the RNA segment sequences into the full-length RNA transcript includes ligation with T4 RNA ligase 2. However, the transcripts generated by T7 RNA polymerase are triphosphorylated and therefore must be "trimmed" to their monophosphorylated analogs before ligation (FIG. 1C). In some embodiments, this is accomplished by treatment of the transcript pool with RNA 5' pyrophosphohydrolase (FIG. 1C), removing a pyrophosphate group from the 5' end of each RNA. In embodiments where monophosphorylated analogs are provided in earlier steps, this trimming step is not necessary. In some embodiments, rNMPs and rNTPs are included at a ratio of about 8:1. In some embodiments, the rNMP to be used is GMP, which is included at a ratio of 8:1 relative to GTP, where the other rNTPs are used at their normal concentration for RNA synthesis. Alternatively, mono-phosphorylated RNA transcripts suitable for ligation may be prepared by manipulations which do not directly remove a pyrophosphate group. For example, calf-intestinal alkaline phosphatase (CIP) may be utilized to remove all phosphates from the in vitro transcribed RNAs, followed by T4 Polynucleotide Kinase, (PNK) treatment to phosphorylate the RNAs prior to the ligation step.

The assembled RNA segments are then ligated with T4 RNA ligase 2 to produce the desired full-length transcript. In this embodiment, the pyrophosphate removal and ligation steps utilize a compatible buffer, which permits them to be performed successively in a single tube without intervening buffer exchange steps and thereby simplifies the overall assembly process. T4 RNA ligase 2 with ATP is thus added directly into the RNA 5' pyrophosphohydrolase-treated reaction, which contains the RNA segments and splints from the oligonucleotide array. The RNA product was reverse-transcribed and PCR amplified using forward and reverse primers for the ZsGreen1 gene. The reverse primer included sequence encoding 6 histidines to enable His-tag purification of the protein product (22).

Based on the inventors' efforts described herein, the invention provides in a first aspect an RNA-mediated assembly method for providing a target RNA molecule. Such a method includes steps of: (a) providing an oligonucleotide array comprised by: (i) a plurality of first surface-bound oligonucleotides each having a segment sequence corresponding to a portion of a target RNA and a complementary RNA Polymerase (RNAP) promoter sequence operably-linked to the segment sequence's 3' termini; and (ii) a plurality of second surface-bound oligonucleotides each having a splint sequence corresponding to a portion of the target RNA that complements and partially overlaps the segment sequence of the first surface-bound oligonucleotides, the second surface-bound oligonucleotides including a RNAP promoter sequence operably-linked to their splint sequence's 3' termini, wherein the first and second surface-bound oligonucleotides are linked at their 3' termini to a surface of the oligonucleotide array; (b) hybridizing a third oligonucleotide encoding a RNAP promoter sequence to the complementary RNAP promoter sequence of the first and second surface-bound oligonucleotides to yield double-stranded RNAP promoters; (c) transcribing with RNA polymerase the segment sequence of the first surface-bound oligonucleotide to yield an RNA segment and the splint sequence of the second surface-bound oligonucleotide to yield an RNA splint; (d) removing any terminal pyrophosphates from the RNA segments and the RNA splints; (e) assembly of the RNA segments and RNA splints by hybridization to form RNA:RNA hybrids; and (f) sealing nicks in the RNA:RNA hybrid to provide a target RNA molecule.

Removal of any terminal pyrophosphates from the RNA segments and RNA splints is carried out using any nucleic acid modifying enzyme suitable for removing such phosphate moieties, such as 5' pyrophosphohydrolase or RNA pyrophosphatase.

Sealing of nicks in the RNA:RNA hybrid is carried out using any nucleic acid modifying enzyme suitable for ligation of RNA, such as T4 RNA ligase 2 or a truncated version thereof.

In certain embodiments, the complementary RNAP promoter sequence operably-linked to the segment sequence and the splint sequence is a complementary T7 RNAP promoter sequence or a complementary T3 RNAP promoter sequence.

In some embodiments the 5' end of each segment sequence and each splint sequence corresponds to a GG dinucleotide in the target RNA molecule.

It is an advantage provided by the invention that steps (d)-(f) in the above-described method may be, at the discretion of the operator, carried out successively without intervening buffer exchange. Such option reduces costs associated with operator labor and time, and costs of reagents and related laboratory materials.

In preferred methods of the invention, the RNA-mediated assembly method is based on a target RNA molecule that is a full-length RNA transcript of a gene such that a full-length DNA encoding the gene may ultimately be obtained in an expedited manner.

In some embodiments, methods utilize surface-bound oligonucleotides which include a spacer, a T7 RNAP promoter sequence, a CC dinucleotide and either the segment sequence or the splint sequence, and particularly preferred embodiments the surface-bound oligonucleotides further include a trinucleotide CTG and a 17 mer T7 RNAP promoter.

In general, the spacer may vary in length and composition, with suitable linker/tethering entities constructed from a wide variety of nucleotide sequences, including, e.g., inverted dT (reverse linkage) sequences. Alternatively, spacers useful in the present methods may be constructed from non-nucleic acid entities, including but not limited to polymers of polyethylene glycol (e.g., PEG18 or PEG2000 spacer arms may be used to substitute the spacer in the exemplary embodiment).

The RNAP promoter sequence contained in the third oligonucleotide can be a T7 RNAP promoter sequence or a T3 RNAP promoter sequence. In some cases, the third oligonucleotide includes a T7 RNAP promoter sequence and a dinucleotide GG, AG, or a single nucleotide (e.g., A). In some embodiments, the third oligonucleotide includes a trinucleotide CTG, a 17 mer T7 RNAP promoter sequence and a dinucleotide GG, AG, or a single nucleotide such as A.

Figure 3:
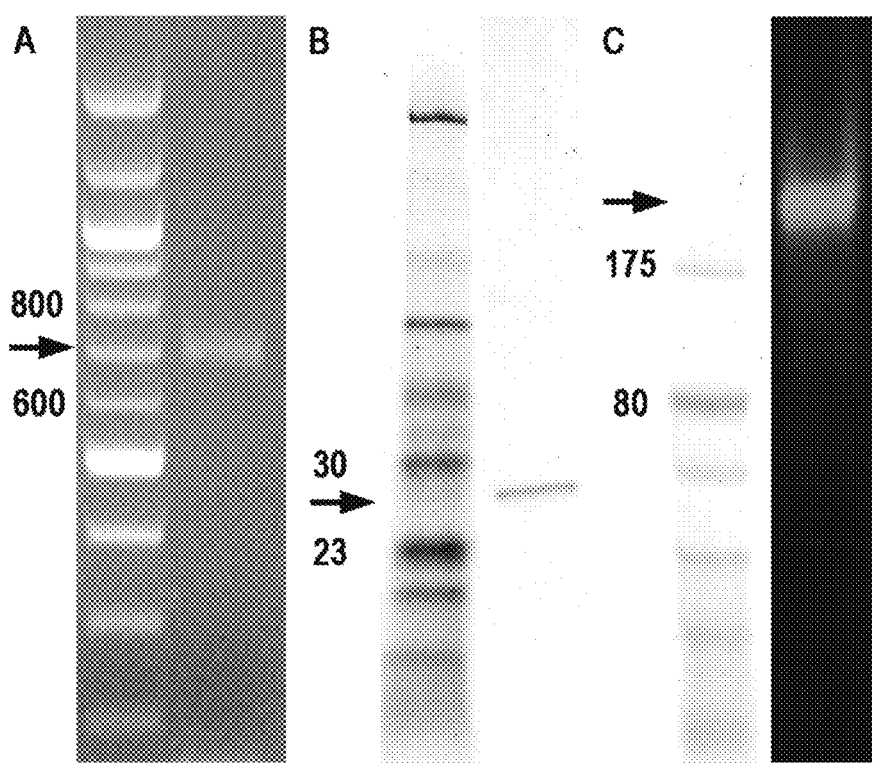
FIG. 3 depicts electropherograms of ZsGreen1 gene and protein synthesized from the RNA assemblies. A) Agarose gel electrophoresis of the product of RT-PCR amplification of the assembled ZsGreen1 transcript with a ZsGreen1 forward primer and a His-tag appended ZsGreen1 reverse primer, along with a 100 bp DNA ladder marker. The expected size is 714 bp. B) Electrophoretic analysis in a "reducing" SDS polyacrylamide gel of the ZsGreen1 protein product obtained in an *E. coli* cell-free expression system from the gene shown in (A). The expected size is 26.9 kDa. C) Electrophoretic analysis in a non-reducing SDS polyacrylamide gel of the same protein product and standard marker set shown in (B). ZsGreen1 exists under non-reducing conditions as a tetramer of theoretical molecular weight 107.6 kDa. It does not migrate true to molecular weight under these non-reducing gel conditions.
Figure 4A:
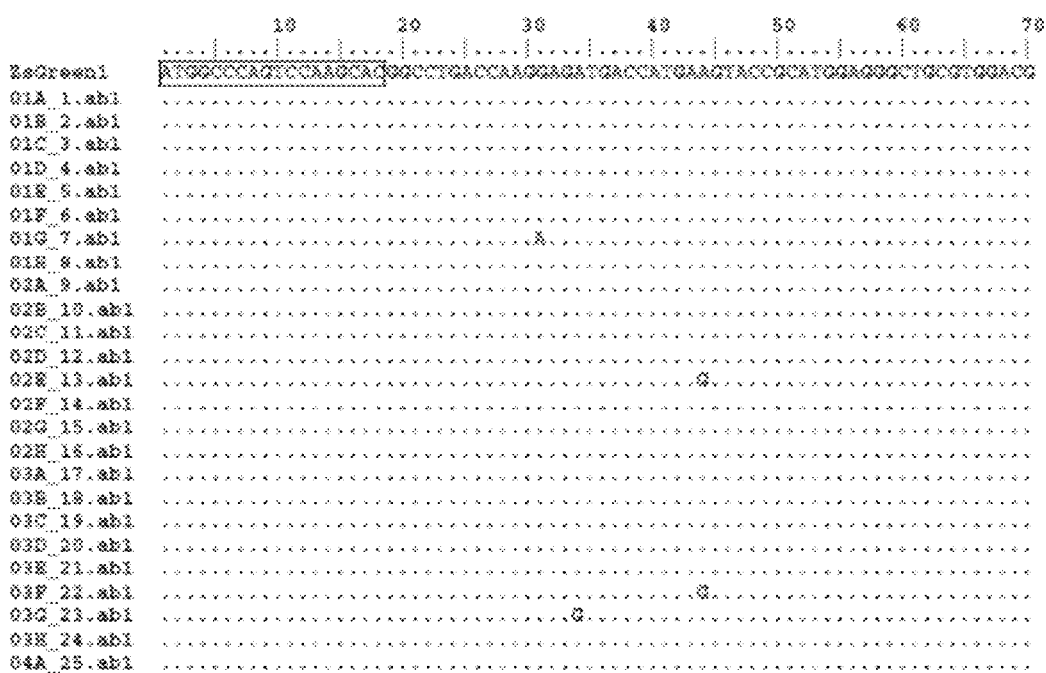
FIG. 4 (A-V) illustrates alignment of Sanger Sequencing Data of ZsGreen1 Assemblies ZsGreen1 gene assemblies from DNA arrays fabricated on either amorphous carbon surfaces (sequence #1 to #25) or on silanized glass surfaces (sequence #26 to #51) were Sanger sequenced (Functional Biosciences, Inc., WI, USA) and aligned with the ZsGreen1 target sequence (SEQ ID NO:82; the 714 nucleotide sequence is shown in its entirety as the top line in FIGS. 4A through 4K, and again as the top line in FIGS. 4L through 4V). It should be noted sequenced nucleotides #1 to #18 correspond to the forward primer sequence (ZsG-F), and sequenced nucleotides #680 to #714 correspond to the reverse primer sequence (ZsG-R-w-6His) for ZsGreen1 RT-PCR amplification. Excluding the primer regions, 16,525 assembled nucleotides from the DNA array fabricated on the amorphous carbon surface were analyzed and 25 transitions, 3 transversions, 1 deletion, and no insertions were identified, which corresponds to an error rate of 0.1755%; whereas 17,186 assembled nucleotides from the DNA array on the silanized glass surface were analyzed and 24 transitions, no transversion, 1 deletion, and 1 insertion were identified, which corresponds to an error rate of 0.1513%. This sequence analysis of cloned constructs indicated a yield of correct constructs of approximately 40%. Analyzing the primer sequences (character bordered), which were conventionally column synthesized from Sigma Aldrich, 1 transitions, 2 transversions, 3 deletions, and 2 insertions were identified in the ZsG-R-w-6His primer region (35 nt long; 1,785 nucleotides were analyzed; corresponds to an error rate of 0.448%) whereas no errors were found in the short ZsG-F primer region (18 nt long).
Figure 4B:
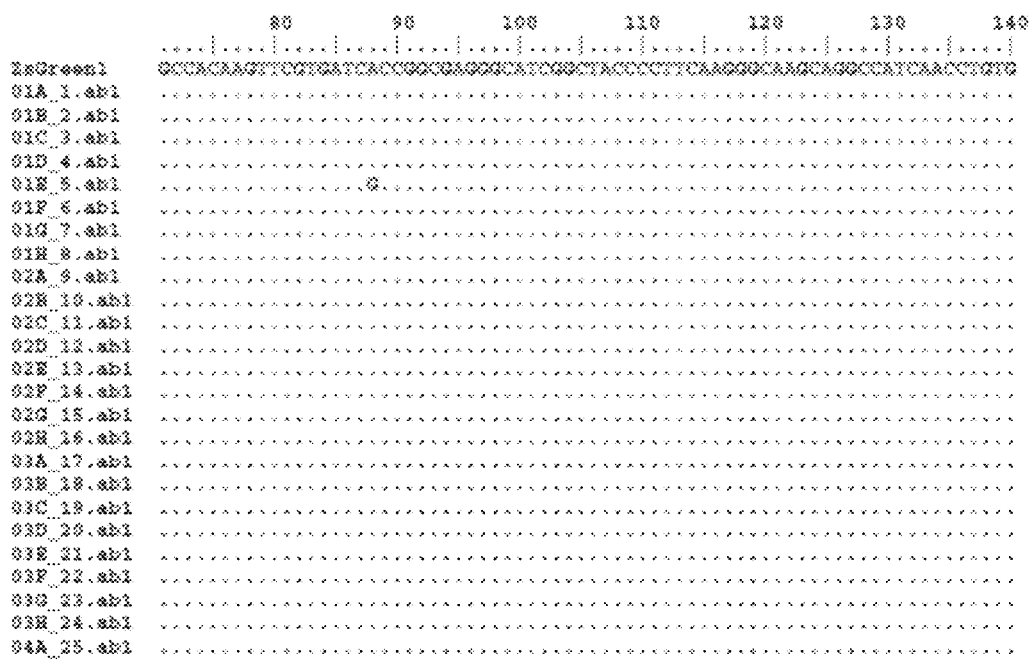
Figure 4C:
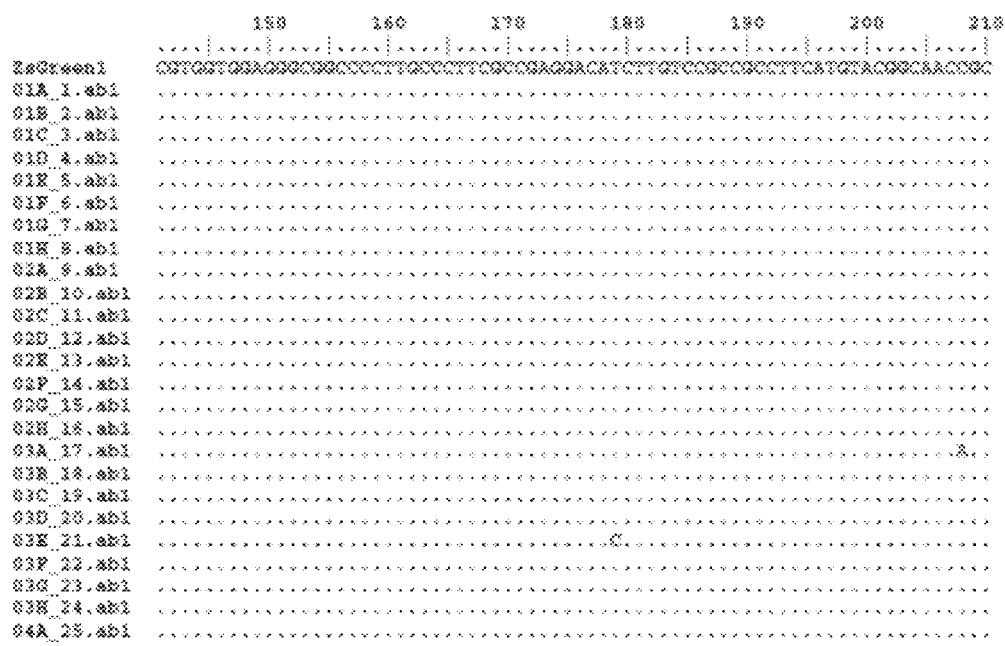
Figure 4D:
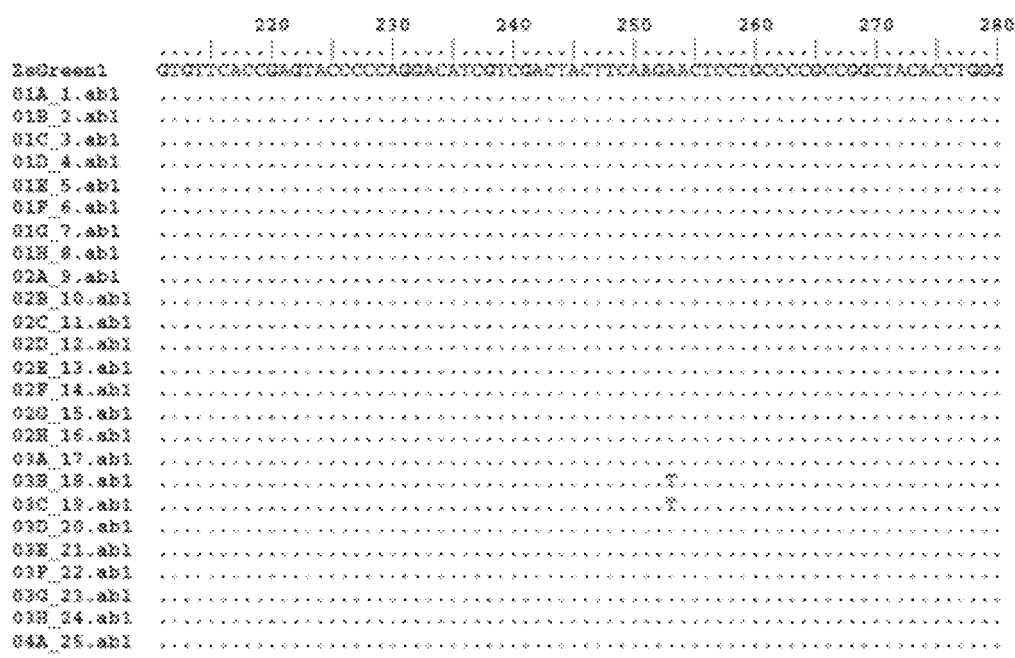
Figure 4E:
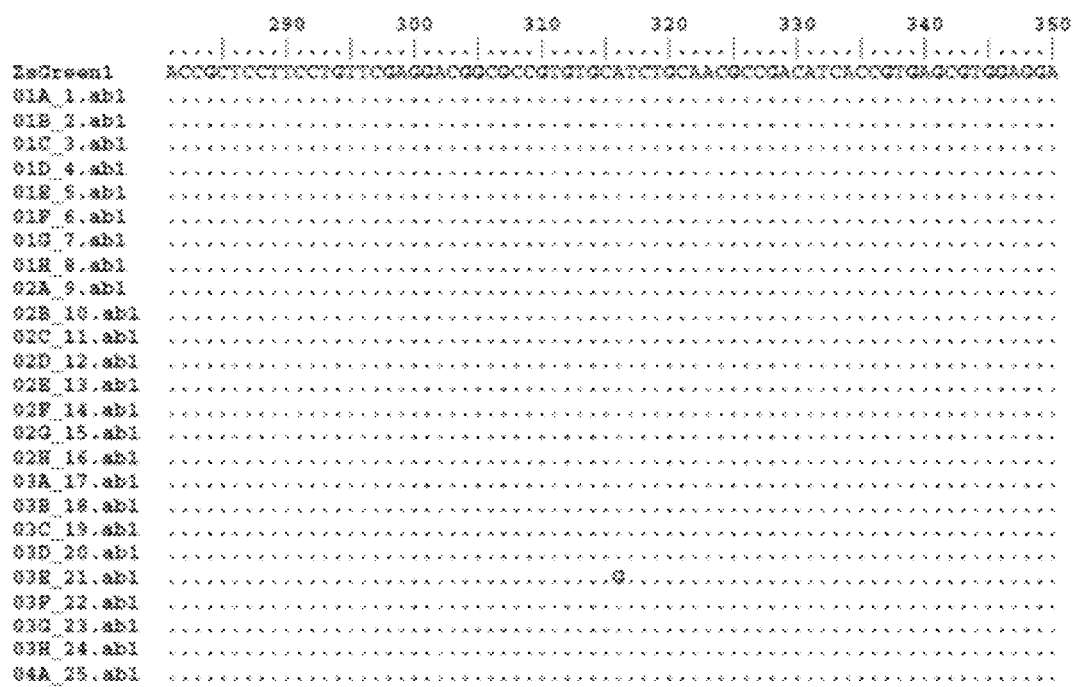
Figure 4F:
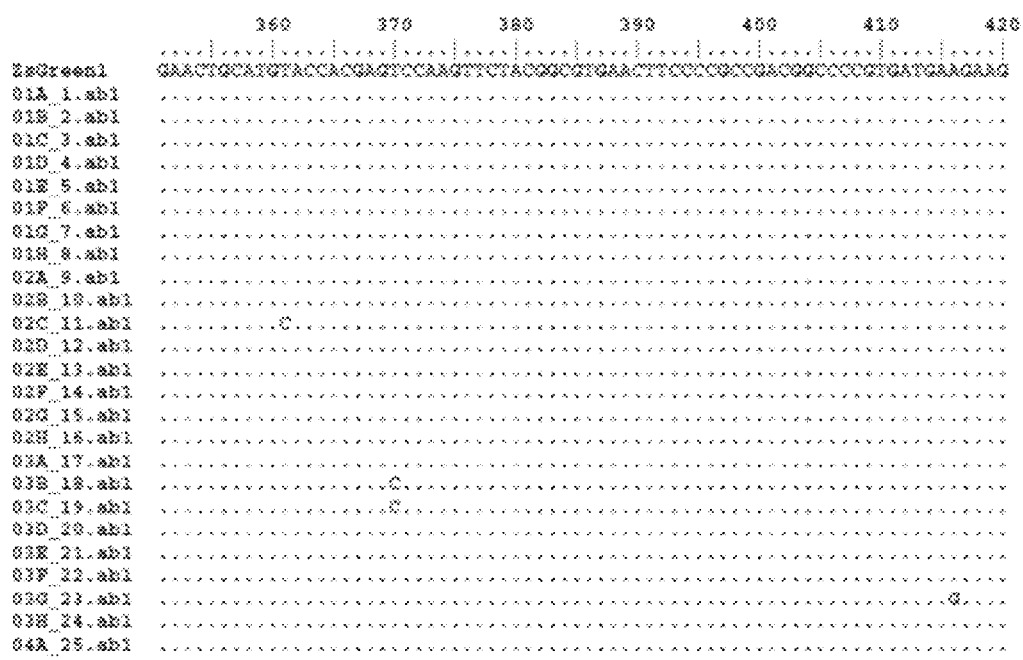
Figure 4H:
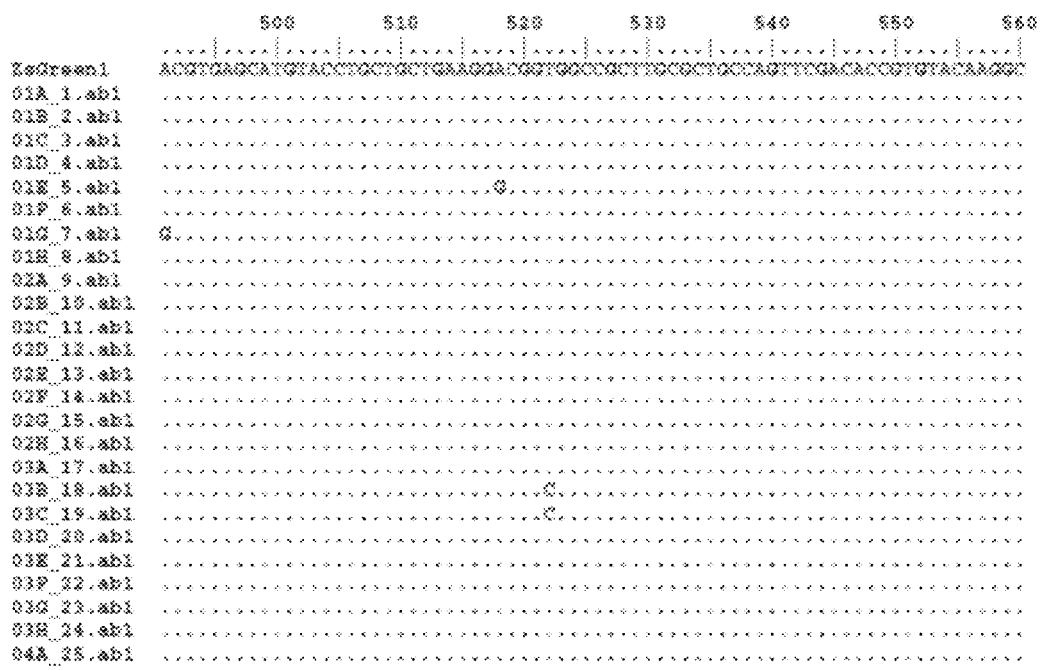
Figure 4J:
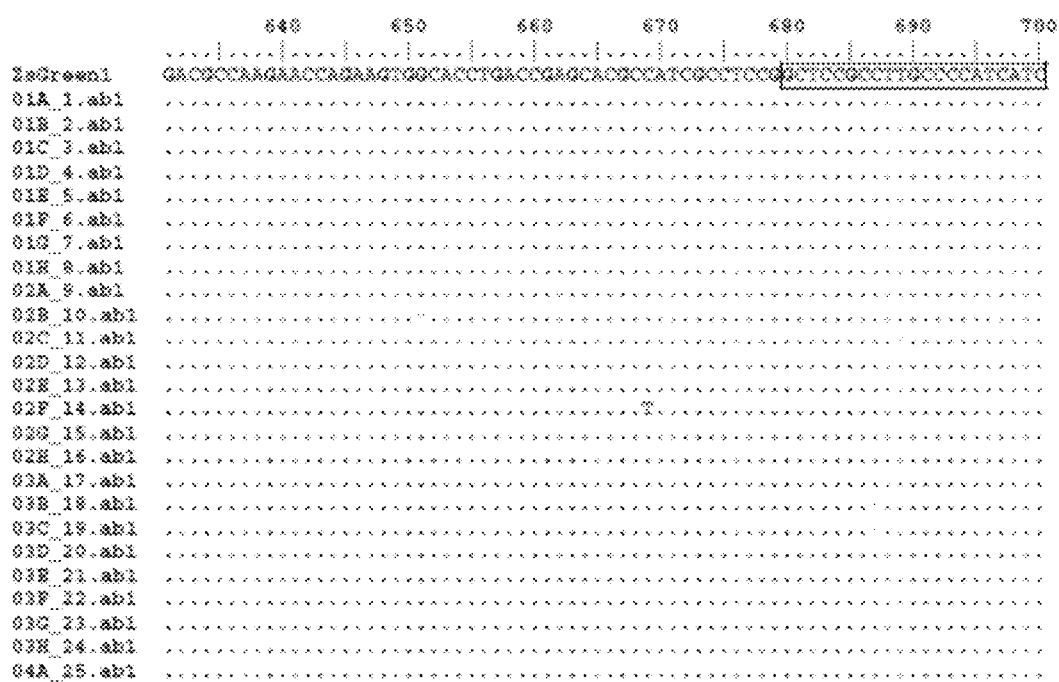
Figure 4L:
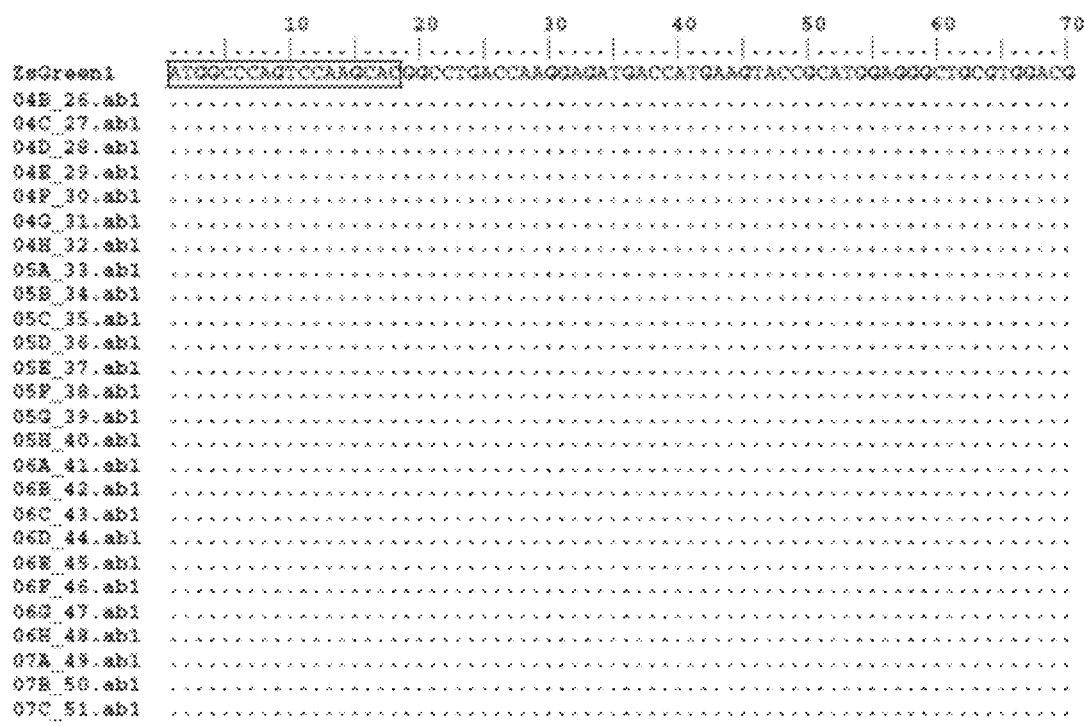
Figure 4N:
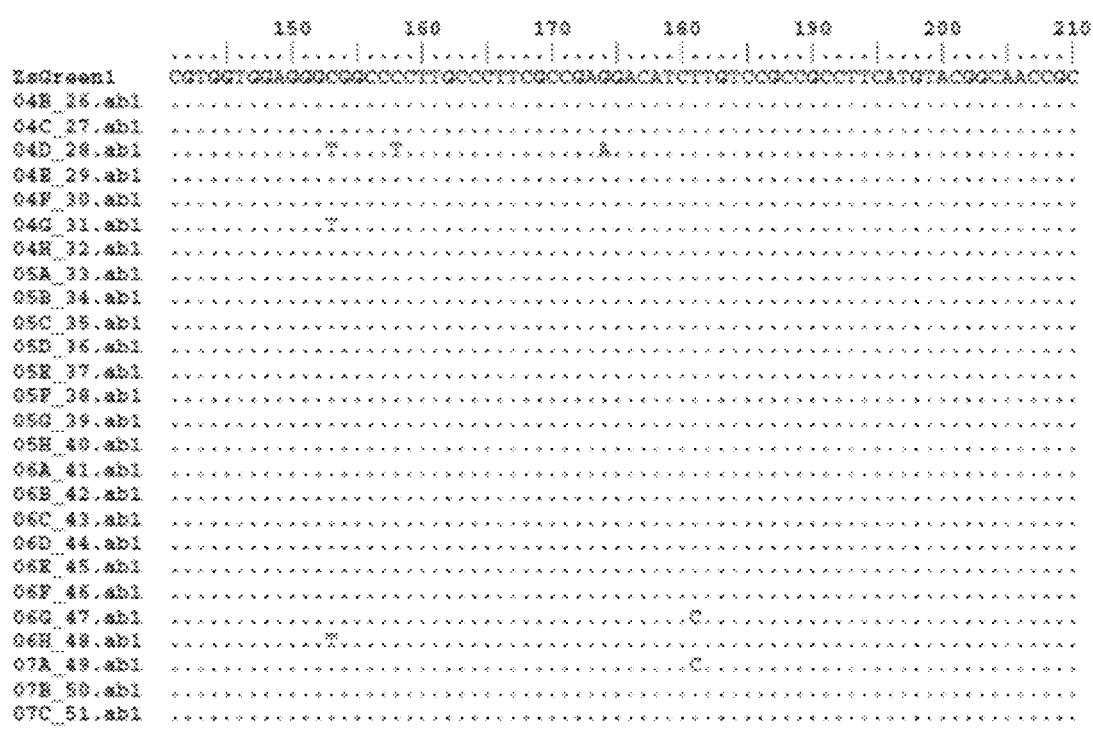
Figure 4O:
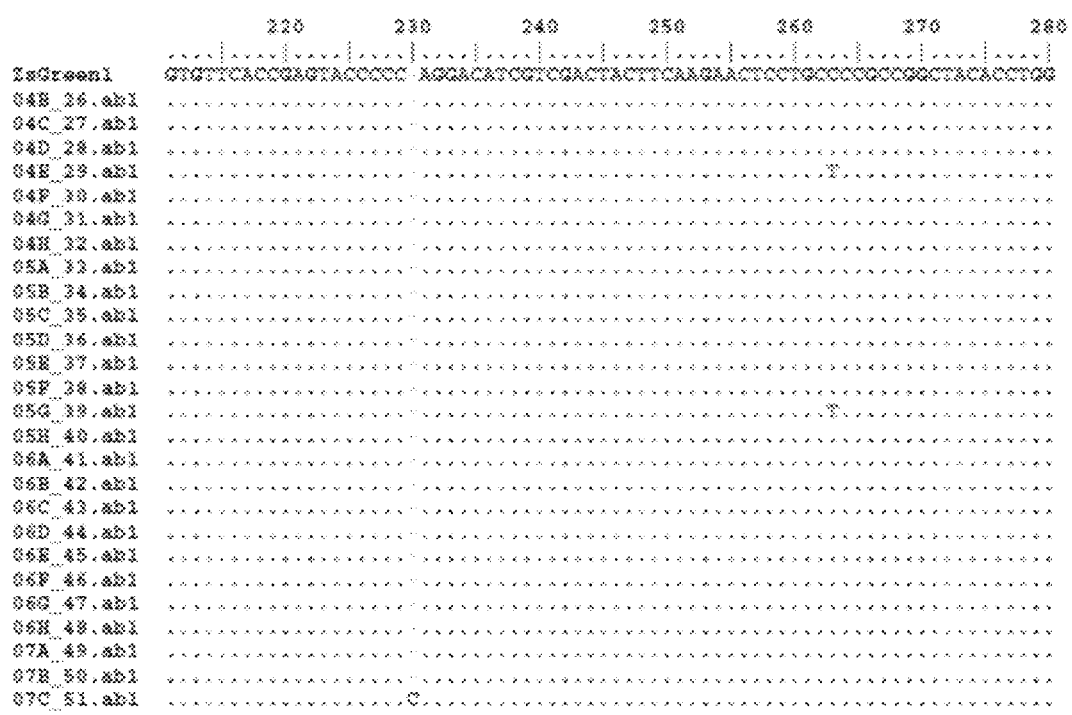
Figure 4P:
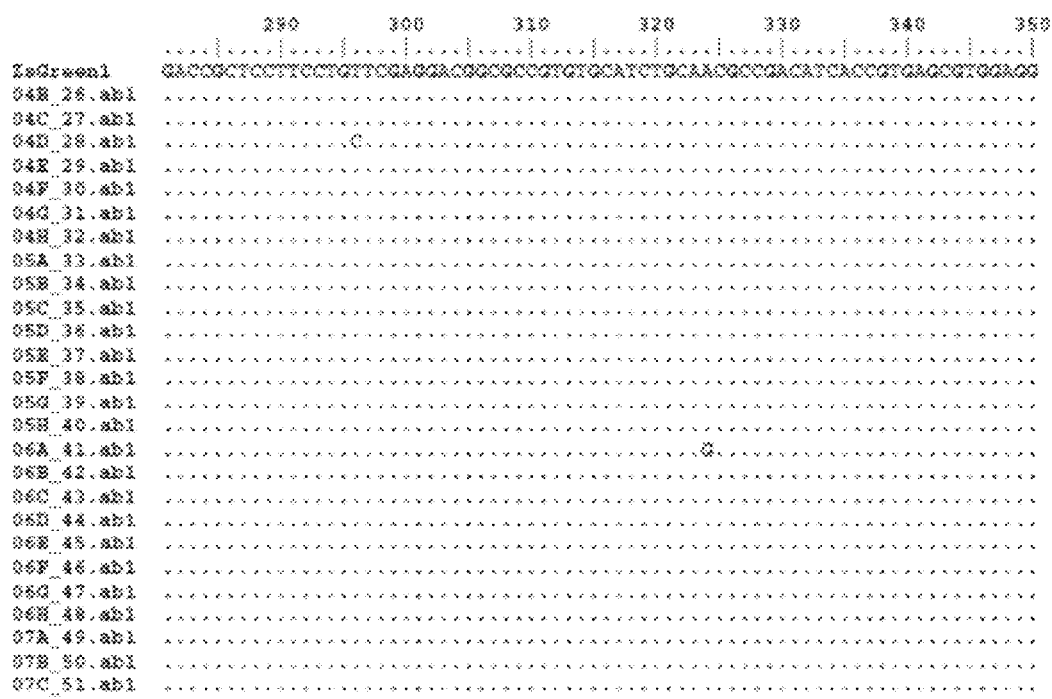
Figure 4Q:
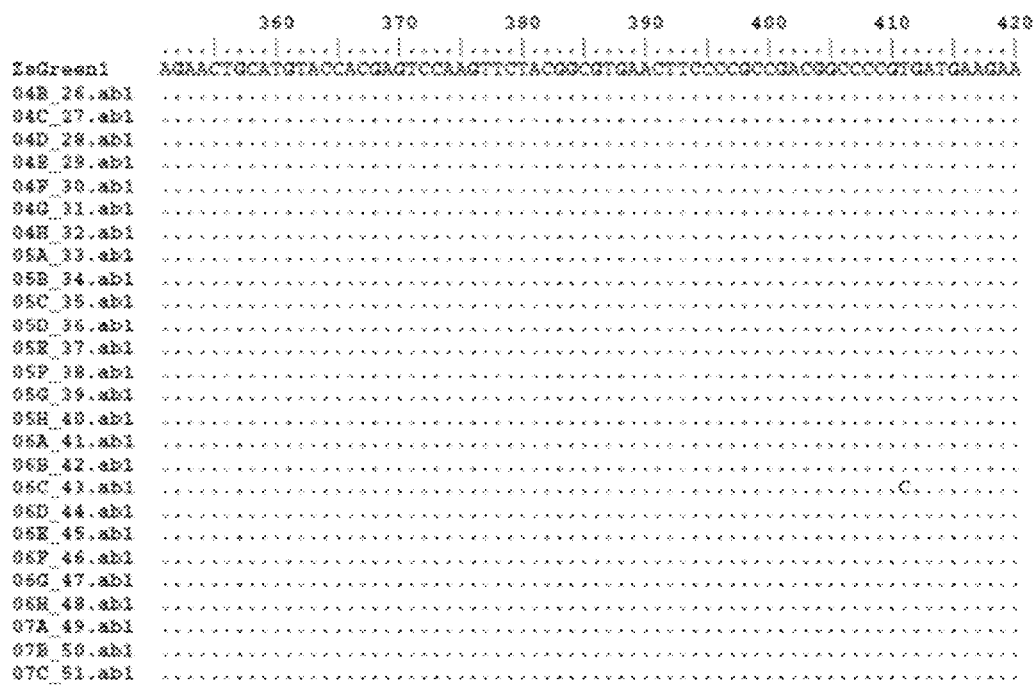
Figure 4R:
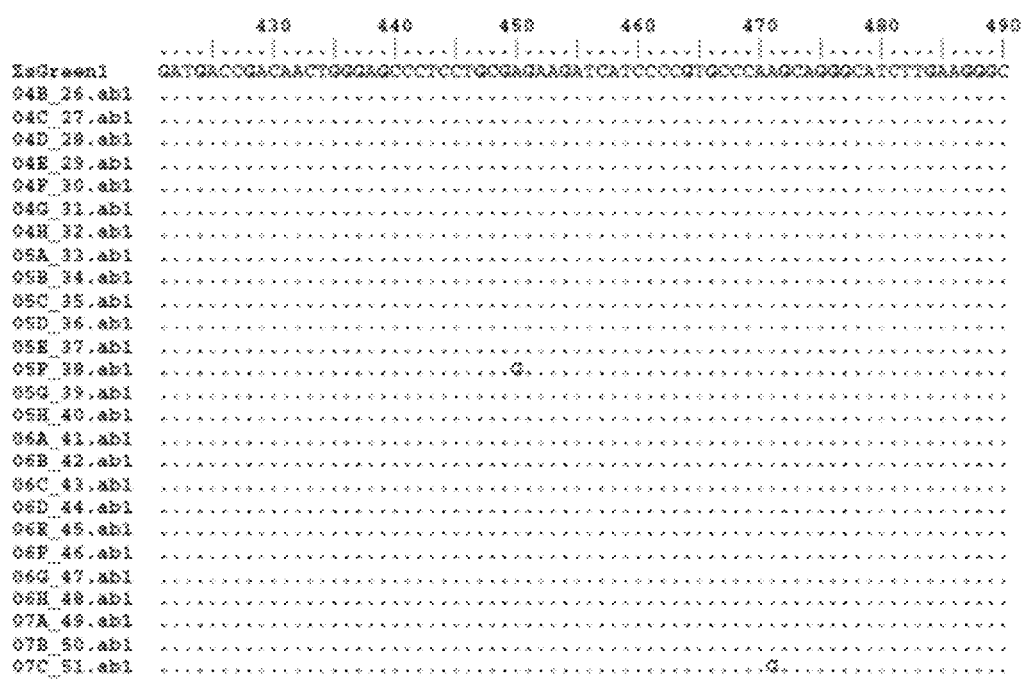
Figure 4T:
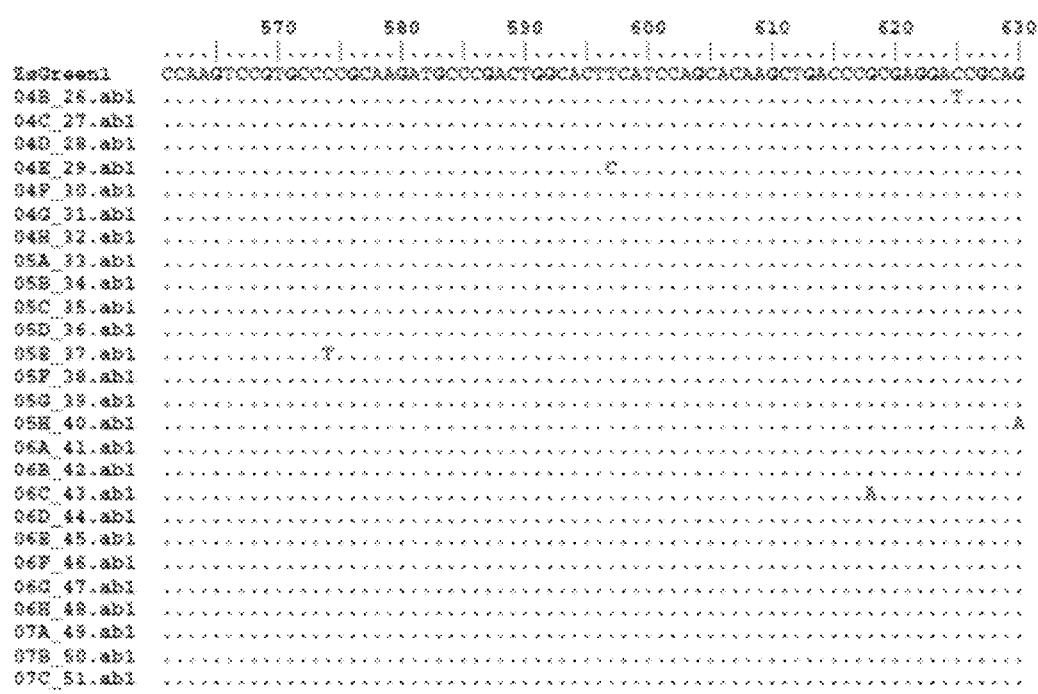
Figure 4U:
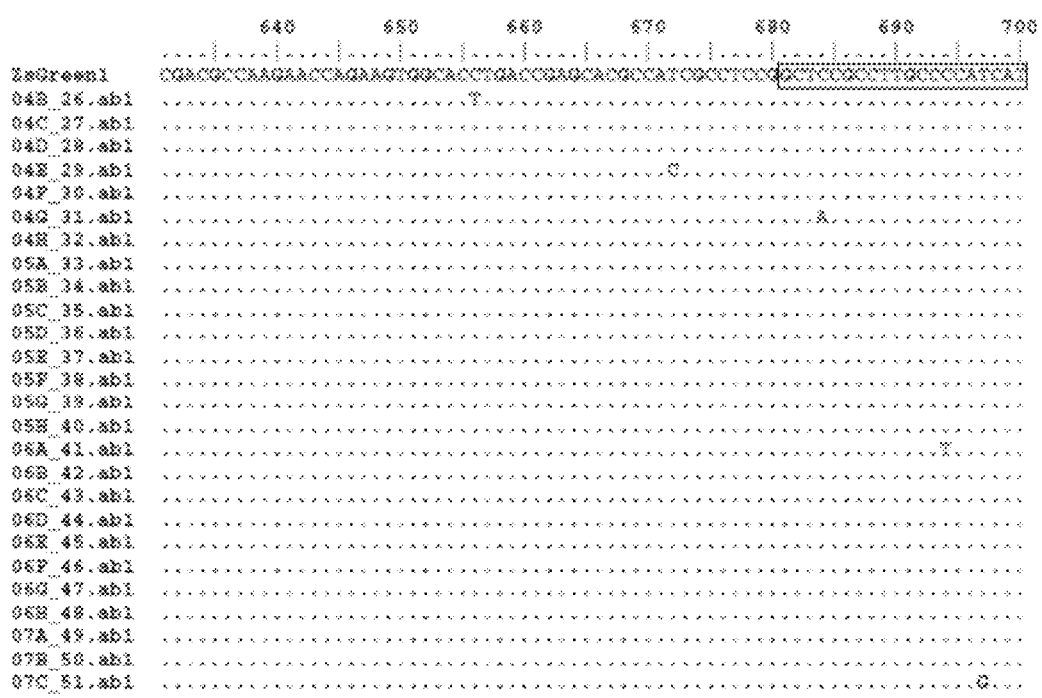

Referring again to the proof-of-principle example, the fidelity of the exemplary assembly process was monitored in four ways. First, the PCR product was analyzed by agarose gel electrophoresis. FIG. 3A shows that a single DNA band of the expected size (714 bp) is obtained. Second, the gene was subjected to in vitro translation and the resultant protein product was analyzed by reducing SDS-PAGE electrophoresis. FIG. 3B shows that only a single band of the expected molecular weight (26,950 daltons) is visible by Coomassie Blue staining. Third, the same protein product was analyzed by non-reducing SDS-PAGE electrophoresis and detected by fluorescence imaging. FIG. 3C shows that only a single fluorescent protein is observed under these non-reducing electrophoretic conditions. Finally, we cloned the PCR product directly (without enzymatic error corrections), and subjected 51 randomly chosen colonies to Sanger sequencing. 22 of the clone sequences were a perfect match to the desired target sequence; in total 33,711 bases of DNA sequence were obtained and 49 transitions, 3 transversions, 2 deletions, and 1 insertion were identified (1.63 errors/kb; see Example Section). This high rate of generation of the correct gene sequence (22/51=~40%) is invaluable for practical applications of gene synthesis technology.

It can be appreciated that the invention contemplates an RNA-mediated gene assembly method for providing a target gene. Such a method includes steps of: (a) reverse-transcribing an RNA target molecule provided by any one of the inventive methods described herein; (b) purifying the target gene.

In a related aspect, the invention provides an RNA-mediated method for providing a target protein. Such a method includes steps of: (a) reverse transcribing an RNA target molecule provided by any one of the inventive methods described herein to provide a target gene; (b) expressing a target protein encoded by the target gene; and (c) purifying the target protein.

In yet another aspect, the invention is directed to the materials used to carry out the present methods, specifically the uniquely-designed oligonucleotide arrays for RNA-mediated assembly of target RNA molecules described herein. Such inventive arrays include: (a) a plurality of first surface-bound oligonucleotides each having a segment sequence corresponding to a portion of a target RNA and a complementary RNAP promoter sequence operably-linked to the segment sequence's 3' termini; and (b) a plurality of second surface-bound oligonucleotides each having a splint sequence corresponding to a portion of the target RNA that complements and partially overlaps the segment sequence of the first surface-bound oligonucleotides, the second surface-bound oligonucleotides including an RNAP promoter sequence operably-linked to their splint sequence's 3' termini, wherein the first and second surface-bound oligonucleotides are linked at their 3' termini to a surface of the oligonucleotide array.

In preferred embodiments, the target RNA molecule is a full-length RNA transcript of a gene.

As noted above, a variety of standard and readily available components and reagents may be utilized in the combination of inventive steps. For example, the oligonucleotide array's surface may be silanized glass or, alternatively, amorphous carbon deposited on a gold film. Accordingly, oligonucleotide arrays useful in the present methods may be provided by any standard fabrication process known in the field including, but not limited to, in situ photolithographic oligonucleotide array synthesis.

In certain embodiments, the complementary RNAP promoter sequence operably-linked to the segment sequence and the splint sequence is a complementary T7 RNAP promoter sequence or a complementary T3 RNAP promoter sequence. In some embodiments the 5' end of each segment sequence and each target sequence corresponds to a GG dinucleotide in the target RNA molecule.

In certain embodiments, arrays include surface-bound oligonucleotides which have a 3' (dT)10 spacer or a PEG 2000 spacer, a CTG trinucleotide, a 17mer T7 RNAP promoter sequence, a CC or other dinucleotide or a single nucleotide and either the segment sequence or the splint sequence.

In certain embodiments, the array includes a third oligonucleotide which has an RNAP promoter sequence complementary to the RNAP promoter sequence of the first and second surface-bound oligonucleotides and which hybridizes with those surface-bound oligonucleotides to yield double-stranded RNAP promoters. The third oligonucleotide, in some embodiments, is a T7 RNAP promoter sequence or a T3 RNAP promoter sequence, more preferably the third oligonucleotide includes a trinucleotide CTG, a 17 mer T7 RNAP promoter sequence and a dinucleotide GG, AG, or the single nucleotide A.

In an alternative set of embodiments, segment sequence and splint sequence oligonucleotides are provided in solution as oligonucleotide libraries, rather than bound to a surface as arrays. The oligo libraries can be similarly used as substrates in the RNA assembly methods described herein.

In further embodiments, multiple target RNAs may be represented, i.e., an oligonucleotide array or library can contain segment and splint sequences directed to the assembly of multiple target RNA assemblies. In such embodiments, the number of represented RNA sequences may range from about 2 to about 100 separate sequences, e.g., 3, 5, 10, 15, 20, 30, 40, 50, 60, 65, 70, 75, 80, 90, or another number of represented RNA target sequences from about 2 to about 100 separate sequences.

In some embodiments, where multiple target RNA sequences are represented, the target RNA sequences contain overlapping complementary ends that allow assembly of the separate RNAs into a longer contiguous sequence. Such longer assembled RNA sequences may range from about 1,000 bases to about 20,000 bases, e.g., about 1,500, 2,000, 2,500, 3,000, 4,000, 5,000, 6,000, 7,000, 10,000, 12,000, 15,000, 17,000, or another sequence length from about 1000 bases to about 20000 bases. In some embodiments, modular and reiterative use of the methods described herein allows assembly of much larger contiguous sequences on the order of 50,000 bases upwards of about 1 million bases, and ultimately to the assembly of synthetic chromosomes by initial assembly of long RNA transcripts, reverse transcription and long range PCR or other DNA amplification methods.

In yet other embodiments, where multiple target RNA sequences are represented in an array, segment and splint oligonucleotides complementary to the same target RNA sequence share at their surface-bound 3' end, in addition to a T7 or a T3 promoter sequence, a shared "tag" sequence of about 10-18 nucleotides, that is uniquely associated with oligonucleotides complementary to the same target RNA to be assembled. To specifically initiate transcription from this subset of oligonucleotides in this array, an oligo comprising both a 5'-sequence complementary to the aforementioned tag sequence and a complementary T7 or T3 RNAP promoter sequence to generate an operable T7 or T3 RNAP promoter sequence is hybridized under stringent conditions so as to hybridize only to the subset of array oligonucleotides containing the corresponding tag sequence. This system allows the use of a single array containing oligo sets for the assembly of RNAs for multiple genes to assemble individual pre-selected RNA targets by simply adding the appropriately tagged-T7/T3 RNAP oligonucleotide.

Previous work on gene assembly from oligonucleotide arrays has employed the DNA sequences themselves, rather than assembling RNA intermediates as employed in this work. The generation of an RNA intermediate has several advantages: (a) ~100 to 1000 copies of the RNA are produced by transcription from each DNA strand present on the array (21); this obviates the need for complex PCR-based oligonucleotide amplification (23) prior to gene assembly (6,7); (b) parallel gene assembly of the RNA segment and splint sequences, directly from the oligonucleotide array, eliminates a number of laborious steps (e.g., cleavage of the oligonucleotides from the array, amplification of the oligonucleotide pool, and purification of the oligonucleotide pool); (c) the sequencing results obtained in the present study show that the full-length RNA transcripts produced have a high sequence fidelity (i.e., a low number of incorrect sequences), whereas the individual oligonucleotides produced during in situ syntheses may include a variety of defects due to side reactions and incomplete nucleotide coupling reactions (24-27). Sequence errors that are present on the array are presumably copied into the RNA transcripts; however, these deleterious sequences may be incorporated less often into the full-length RNA transcripts due to the additional sequence fidelity constraints innate to the hybridization/ligation assembly procedure. (d) The assembled product is an RNA transcript that is readily copied into DNA for cloning or for production of more RNA copies by in vitro transcription. The RNA-mediated assembly process described here is also considerably simpler and more rapid than previously described multi-step and multi-day strategies (6,7), involving only four successive enzymatic procedures that are readily performed in a few hours. Referring to Table 1 below, we compare here the RNA-mediated assembly technology with other recently published gene assembly technologies. The RNA-mediated strategy drastically reduces the time and labor required for high fidelity gene synthesis from weeks to a days and no specialized equipment is needed (not including the array fabrication). As can be appreciated, the present invention provides an avenue to the assembly in a step-wise manner of large gene clusters, chromosomes, and even eventually genomes.

TABLE 1

| Comparison of selected strategies for gene assembly from DNA arrays | | |
| --- | --- | --- |
| Kosuri et al. (7) | Matzas et al. (6) | Wu et al. (this study) |
| Production of oligonucleotide library (Agilent OLS) (proprietary synthesis, cleavage and amplification. 7 d)* | Cleavage of oligos from the arrays, and purification. | T7 RNA amplification from the array (4 h~12 h)* |
| Assembly-specific PCR amplification (2 h)* | Amplification with emulsion PCR | Buffer exchange (1 h)* |
| Purification for size verification | Sequencing with next generation sequencer | Pyrophosphate removal (2 h)* |
| Reamplification in 20 mL with chemically modified assembly-specific primers | Sequences selected and localized | T4 RNA ligation to produce full-length RNA transcript (40 min)* |
| Split into 96 well plates | Bead extraction with a micro actuator from a picotiter plate to 96-well plate | Reverse transcription PCR for full-length coding gene (3 hr)* |
| Buffer exchange (cleanup) | Amplification of DNA individually from beads. Variable biotinylated primers used to remove restriction products containing biotin residues by streptavidin matrix. | |
| Protease digestion followed by heat inactivation | Gel purification-estimation of oligo concentration and mixing the amplicons in equimolar amounts | |
| Protein removal | Removal of primer regions | |
| Buffer exchange (cleanup) | Ethanol precipitated | |
| Lambda exonuclease digestion | Polymerase cycling assembly | |
| Buffer exchange | | |
| DpnII digestion and USER enzyme (NEB) with guide oligo | | |
| Buffer exchange (cleanup) | | |
| Polymerase cycling assembly (4 h)* | | |
| Error correction (3.5 h)* | | |
| Column reaction cleanup | | |
| Restriction digestion (2 h)* | | |
| Gel purification (2 h)* | | |

We have described here, by reference to an exemplary embodiment, a strategy for the RNA-mediated assembly of full-length RNA transcripts and, subsequently, a gene from DNA arrays. Proof-of-principle was demonstrated in the assembly of a small gene encoding the green fluorescent protein ZsGreen1, and its in vitro translation to yield a functional protein. Sequence analysis of cloned constructs indicated a yield of correct constructs of approximately 40%.

Beyond gene assembly, the present invention is also useful for the preparation of multiple copies of target RNA molecules, including RNA pools/libraries. Such oligonucleotide array-based method to provide target RNA molecules include steps of: (a) providing an oligonucleotide array comprised by a plurality of surface-bound oligonucleotides each having a segment sequence corresponding to a portion of a target RNA and a complementary RNAP promoter sequence operably-linked to the segment sequence's 3' termini; (b) hybridizing an oligonucleotide encoding a RNAP promoter sequence to the complementary RNAP promoter sequence of the surface-bound oligonucleotides to yield double-stranded RNAP promoters; and (c) transcribing the segment sequence of the surface-bound oligonucleotide that corresponds to the portion of the target RNA sequence with RNA polymerase to yield multiple copies of a target RNA molecule. In preferred embodiments, a pool of target RNA molecules differing in nucleotide sequences is provided by the method.

In a related aspect, the invention provides oligonucleotide arrays useful for carrying out the methods described in the preceding paragraph. Such oligonucleotide arrays include a plurality of surface-bound oligonucleotides each having a segment sequence corresponding to a portion of a target RNA and a complementary RNAP promoter sequence operably-linked to said segment sequence's 3' termini. In certain embodiments, the arrays further include an oligonucleotide encoding a RNAP promoter sequence hybridized to the complementary RNAP promoter sequence of the surface-bound oligonucleotides to yield double-stranded RNAP promoters. As can be appreciated, the presently-described arrays find a variety of uses where multiple copies of RNA molecules are required. Accordingly, this aspect of the invention may be utilized, with no more than routine modification, to prepare a variety of RNA-based or related molecules, such as catalytically-active RNAs (i.e., ribozymes). Alternatively, the inventive methods are useful for providing pools/libraries of RNA molecules, such as, e.g., microRNA or siRNA libraries to be screened for desirable bioactivities/functionalities, or, alternatively, for preparing RNA-based probes, including, but not limited to, biotinylated, radio-labeled and fluoro-labeled nucleic acid probes useful in a variety of detection/imaging applications.

In certain embodiments, the oligonucleotide arrays are provided in the form of a plurality of beads with the above-described oligonucleotides bound to the surface of such beads covalently or non-covalently.

The following examples are offered for illustrative purposes only, and are not intended to limit the scope of the present invention in any way. Indeed, various modifications of the disclosed method in addition to those shown and described herein will become apparent to those skilled in the art from the foregoing description and the following examples and fall within the scope of the appended claims.

III. Examples

Example 1 Generation of Translation-Competent zsGreen RNA by Microarray-Mediated RNA Assembly Materials and Methods Design of DNA Arrays for RNA-Mediated Assembly The full-length ZsGreen1 coding gene plus Kozak sequence (696 nt RNA transcript encoding ZsGreen1, and 10 additional nucleotides corresponding to the Kozak sequence for eukaryotic cell-free expression system) was split into 18 segments. Segments were designed to include terminal GG dinucleotides to enhance in vitro T7 RNA polymerase transcription. Every segment is longer than 30 nt to provide a minimum of 15 bp hybridization with the splint oligos. Splint RNAs were appended with an initial GG dinucleotide for the same reason as for the target fragments. 37 single stranded DNAs were synthesized on the microarray (see sequence information for details), which includes 18 segment RNA templates, 17 splint RNA templates, and two control oligos for quality monitoring. For each of the 9 longest segment sequences (>67mer), multiple features were made rather than just one, in order to increase the amount of RNA produced (see "sequences on the microarray" below). Each feature is sized 1680 µm×1232 µm.

Preparation of Substrates for In Situ Photolithographic Oligonucleotide Array Synthesis Silanized glass. Glass is the standard substrate for DNA array fabrication because of its advantages of low intrinsic fluorescence, non-porosity and ease of modification using silane chemistries. Glass microscope slides (Plain Micro Slides, VWR, PA, USA) were cleaned with 1M sodium hydroxide prior to silanization. The slides were then silanized for 4 h in 2% (v/v) N-(2-triethoxysilylpropyl)-4-hydroxy-butyramide (Gelest, Inc., Morrisville, Pa., USA) in stock solution (0.1% acetic acid in 95% ethanol). After being rinsed by stirring in fresh stock solution for 15 min, the slides were transferred to a pre-heated (120° C.) oven for 2 h, and cured under vacuum overnight.

Carbon-on-gold. In addition to the use of the above standard glass substrates for DNA array fabrication, we also employed substrates overlaid with amorphous carbon deposited on a gold thin film because of their superior thermal stability (18). Tetraethylene glycol monoallylether was employed for the preparation of hydroxyl terminated surfaces for photolithographic oligonucleotide array synthesis since it has been reported that polyethylene glycol modified surfaces help to reduce nonspecific adsorption of proteins (28). First, standard glass slides coated with 50 Å chromium and 1,000 Å of gold (EMF corp., NY, USA) were extensively rinsed with hexane and ethanol and dried under a nitrogen stream. A 7.5 nm layer of amorphous carbon was then DC magnetron sputtered on the gold surface (Denton Vacuum, NJ, USA). 40 µL of tetraethyleneglycol monoallylether, which was synthesized according to a literature procedure (29), was placed directly onto the amorphous carbon surface, and then covered with a quartz coverslip. The surfaces were irradiated under nitrogen purge with a low-pressure mercury vapor quartz grid lamp ($\lambda$=254 nm, 0.35 mW/cm2) for 16 h. After the photoreaction, the surfaces were rinsed extensively with ethanol and deionized water and dried under nitrogen.

In Situ Photolithographic Oligonucleotide Array Synthesis

Light-directed photolithographic synthesis of DNA arrays was performed on either the silanized glass slides or the ethylene glycol modified carbon-on-gold surface with a digital micromirror-based Maskless Array Synthesis (MAS) system connected to a ABI Expedite™ 8909 Nucleic Acid Synthesis System (Applied Biosystems, CA, USA) as described previously (4,17,30). Oligonucleotide synthesis reagent, 0.1M Activator 42 (5-[3,5-Bis(trifluoromethyl)phenyl]-1H-tetrazole) and all NPPOC (3'-nitrophenylpropyloxycarbonyl) protected phosphoramidites [5'-NPPOC-dAdenosine (tac) 3'-$\beta$-cyanoethylphosphoramidite (NPPOC-dA), 5'-NPPOC-dThymidine 3'$\beta$-cyanoethylphosphoramidite (NPPOC-dT), 5'-NPPOC-dCytidine (ib) 3'$\beta$-cyanoethylphosphoramidite (NPPOC-dC), 5'-NPPOC-dGuanosine (ipac) 3'$\beta$-cyanoethylphosphoramidite (NPPOC-dG)] were purchased from Sigma Aldrich. Anhydrous wash (acetonitrile), amidite diluent (acetonitrile), capping reagent A (THF/PAc2O), capping reagent B (Cap Mix B 10% N-Methylimidazole in THF) and deblocking mix (3% dichloroacetic acid in dichloromethane) were purchased from Glen Research (VA, USA). Oxidizing reagent (0.02 M iodine in THF/pyridine/H2O, 89.6/0.4/10) was purchased from EMD Chemicals (NJ, USA). Exposure solvent is 1% imidazole in DMSO. Anhydrous reagents were kept over molecular sieves (AldraSORB™ water trapping packets, Sigma Aldrich). The oligonucleotide synthesis protocol was modified and optimized based on previously published protocols. (18,20) Briefly, every synthesis cycle contains two capping steps to achieve high yield of full-length templates and one oxidation to stabilize the phosphodiester bonds. The step-sequence was coupling (80 sec), capping (20 sec), oxidizing (15 sec), capping (flow though), and UV deprotection. The light dose to remove the photolabile NPPOC (3'-nitrophenylpropyloxycarbonyl)-protecting groups from NPPOC phosphoramidites (Sigma Aldrich, MO, USA) was determined prior to DNA array fabrication. A series of incremental doses of 365 nm light (Joule/cm2) was used for a 30 nt quality control (QC) oligonucleotide synthesis. The optimal dose was chosen to yield the highest level of fluorescence from hybridization of a fluorescently tagged QC complement. It is noted that the complete removal of NPPOC protecting group is important to eliminate possible deletions during synthesis. Array synthesis proceeded as follows: (a) after coupling of the previous NPPOC-protected base to the growing DNA strand, the synthesis flow cell (volume~100 μl) was flushed with 500 μl of exposure solvent; (b) a digital image (mask) representing the locations for the next base addition illuminated the surface with either 4.2 Joule/cm2 of 365 nm light on silanized glass or 3.5 Joule/cm2 of 365 nm on carbon surface using a 350 watt mercury arc lamp (Newport, Conn., USA). Exposure solvent was constantly flowed through the flow cell at a rate of 180~220 μl/(Joule/cm2) during illumination, sufficiently maintaining the basic conditions needed to drive the photocatalyzed elimination reaction. (31) (c) Following irradiation, the array was washed with acetonitrile (~400 μk) to remove residual exposure solvent, dry wash (~300 μl) to remove trace water, and activator solution (~100 μl). (d) Coupling of the next base was achieved by filling the flow cell with a 1:1 solution of the desired phosphoramidite and Activator 42. All 5'-NPPOC-protected amidites underwent a single 80s coupling step. (e) After amidite coupling, the array was capped with a 1:1 v/v mixture of capping reagents A and B (A:B solution) for 20 sec (~320 μl). (d) After washing with acetonitrile (~100 μl) the array was oxidized with oxidizer solution for 15 sec (THF, pyridine, iodine, and water; ~480 μl). (e) A second capping step was performed by flushing the cell with capping reagent A:B solution. (f) After synthesis is complete, the nucleoside bases are deprotected in 1:1 ethylenediamine:absolute ethanol solution at room temperature for 2 hr. The primary significant differences from previously published protocols (18,20) are: (i) a higher photo dose was used to remove the NPPOC-protecting groups on the carbon-on-gold surface; (ii) a longer coupling time (80 sec) and different activator (Activator 42) were used; (iii) capping was conducted directly after each amidite coupling followed by oxidation and another capping step; (iv) An oxidizing step was included in every cycle.

On-Chip RNA Transcription with T7 RNA Polymerase

A gasket, Gene Frame—15×16 mm internal (Abgene, Epsom, UK), was attached and surrounded the DNA features. A 100 μl total in vitro RNA transcription reaction contains a final concentration of 2.25 U/μl T7 RNA polymerase-Plus™ (Ambion, Tex., USA), 0.8 mM each NTP, 1 μM T7RNAP promoter complement, 1x RNAsecure™ reagent (Ambion, Tex., USA), 20 mM NaCl, 40 mM Tris pH 7.8, 6 mM MgCl2 2 mM spermidine, and 10 mM DTT. The reaction mixture, except T7 RNA polymerase, was applied to the chip and incubated at 60° C. for 10 min, then slowly cooled down to room temperature. T7 RNA polymerase was then added to the surface. The transcription reaction was conducted at room temperature for 4~12 hr in a humid chamber. The total reaction was collected and desalted three times with deionized water using a cellulose-based 3,000 molecular weight cut-off Amicon Ultra-0.5 mL centrifugal filter (Millipore, Mass., USA) prior to pyrophosphate removal.

Pyrophosphate Removal from Triphosphorylated RNA Transcripts

RNA transcripts initiated with triphosphorylated GG dinucleotides were treated with RNA 5' Pyrophosphohydrolase (RppH) (NEB, MA, USA) in amended T4 RNA ligase 2 reaction buffer (without ATP) instead of 1×NEBuffer 2 (NEB) to reduce the possibility of losses due to extra steps, and to simplify the overall assembly process. 5 units of RppH were used to remove pyrophosphate group in a half volume of buffer exchanged RNA transcription reaction in a final concentration of 50 mM Tris-HCl pH7.5, 2 mM MgCl2, and 1 mM DTT. The reaction was incubated at 37° C. for 2 hr in a total volume of 25 μl.

Full-Length RNA Ligation with T4 RNA Ligase 2

10 units of T4 RNA ligase 2 and a final concentration of 800 μM ATP were added to the RppH treated reaction above (a half of the total on chip transcribed RNAs.) The ligation reaction involved an initial ligation step at 37° C. for 10 min, followed by 3 cycles of thermal-cycled ligation at 65° C. for 30 sec and 37° C. for 5 min, and finished with a final ligation step at 37° C. for 10 min.

10 units of T4 RNA ligase 2 and a final concentration of 800 μM ATP were added to the RppH treated reaction above (a half of the total on chip transcribed RNAs.) The ligation reaction involved an initial ligation step at 37° C. for 10 min, followed by 3 cycles of thermal-cycled ligation at 65° C. for 30 sec and 37° C. for 5 min, and finished with a final ligation step at 37° C. for 10 min. The reaction temperature for ligation could also be at a fixed temperature of 37° C. for 50 min.

In some cases, the guanosine-initiating T7 class III promoter phi 6.5 is replaced with the adenosine-initiating T7 class II promoter phi2.5 to decrease 5' heterogeneity of RNA transcripts. In addition, the replacement of T7 RNA promoter provides certain degree of flexibility for experiment design, i.e., segment and splint RNAs will be free of restriction to initiate with guanosine. Also, the penultimate deoxyribonucleotide of DNA template could be replaced with a C2' methoxy RNA ribonucleotide to reduce 3' heterogeneity of RNA transcripts in a transcription reaction, which is deleterious to specific RNA ligation reactions in this method.

Figure 5:
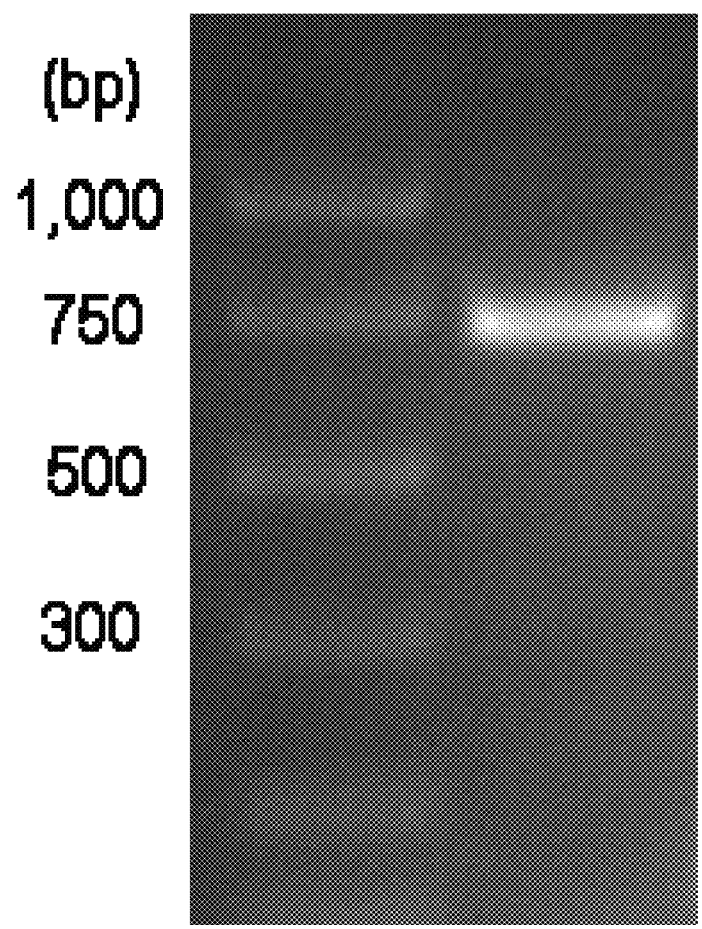
FIG. 5 shows images of RT-PCR product bands separated by agarose gel electrophoresis. The in vitro transcription reaction for segment and splint RNAs utilized a final concentration of 0.8 mM GMP, 0.1 mM GTP, 0.5 mM ATP, 0.5 mM CTP and 0.5 mM UTP along with its reaction buffer and T7 RNA polymerase. The reaction mixture, after buffer exchange, was directly subjected to a ligation reaction with T4 RNA ligase 2. Following the RNA ligation, the assembled RNA (743 nt) was then RT-PCR amplified with a pair of mWasabi specific primers for a 708 bp long mWasabi gene. The product was analyzed in 2% agarose gel along with a PCR DNA marked ladder (Promega, Wis.).

In some cases, pyrophosphate removal from triphosphorylated RNA transcripts is not necessary. The 5' monophosphorylated RNA transcripts can be prepared by including excess guanosine monophosphate (GMP) in the transcription reaction. GMP is only incorporated at 5'-end of the transcript. Ideally, a high proportion of 5' monophosphorylated RNA transcript will result from skewing the ratio of GMP to GTP, e.g., at a ratio of GMP to GTP of 8:1. The product is then subjected to a ligation reaction with T4 RNA ligase 2, as shown in FIG. 5. An example was provided (Figure ?).

Reverse Transcription PCR for Assembled RNA Transcripts

Assembled ZsGreen1 RNA transcripts for cloning and prokaryotic cell-free protein expression were amplified by reverse transcription PCR (RT-PCR) using a OneStep RT-PCR Kit (QIAGEN, CA, USA). ZsGreen1 specific primers, ZsG-F and ZsG-R-w-6His were used (see Sequence Information for details). Cycling consisted of 30 min at 50° C., 15 min at 95° C.; then 40 cycles of 30 sec at 95° C., 30 sec at 61° C., and 1 min at 72° C.; and final elongation 10 min at 72° C.

Assembled ZsGreen1 RNA transcripts for eukaryotic cell-free protein expression were amplified by RT-PCR using a GeneAmp Gold RNA PCR Reagent Kit (Applied Biosystems, CA, USA). ZsGreen1 specific primers: ZsG-F and ZsG-R were used. Cycling consisted of 12 min at 42° C., 10 min at 95° C.; then 45 cycles of 20 sec at 94° C., 20 sec at 58° C., and 30 min at 72° C.; and final elongation 7 min at 72° C. The ZsGreen1 DNA was gel purified. Next, T7-ZsG-F and ZsG-R primers were used to append a T7 promoter to ZsGreen1 coding gene. Phusion Hot Start High-Fidelity DNA Polymerase (NEB) was used. Cycling consisted of 30 sec at 98° C.; then 35 cycles of 10 sec at 98° C., 20 sec at 62° C., and 30 sec at 72° C.; and final elongation 10 min at 72° C.

The RT-PCR products were analyzed by electrophoresis in a 1.5% agarose gel along with a 100 bp DNA ladder (NEB).

Cell-Free Protein Expression, Purification and Detection
Prokaryotic Cell-Free Protein Expression.

The assembled ZsGreen1 gene without Kozak sequence was ligated to pEXP5-CT/TOPO vector (Invitrogen, OR, USA) followed by transformation into ONE Shot TOP10 Competent *E. coli* cells (Invitrogen). The plasmids with inserts were purified with a QIAprep Spin Miniprep Kit (QIAGEN). One microgram of plasmid DNA was used in a standard 100 µl reaction of Expressway Mini Cell-Free *E. coli* Expression System (Invitrogen). The protein expression reaction was performed for 4 hr at 30° C. ZsGreen1 protein was either directly analyzed in protein gels or purified with Ni-NTA Magnetic Agarose Beads (QIAGEN) prior to the analysis.

Eukaryotic Cell-Free Protein Expression.

ZsGreen1 RNA transcripts with Kozak sequence were produced from assembled T7 promoter appended ZsGreen1 gene by using a MEGAscript T7 kit (Ambion). The transcription reactions were buffer exchanged with water using a cellulose-based 30,000 molecular weight cut-off Amicon Ultra-0.5 mL centrifugal filter. Approximately 3.7 micrograms of RNA transcripts were used in a 20 µl Retic Lysate IVT (Ambion) cell-free expression reaction.

Protein Analysis.

The protein products obtained from the in vitro expression system were analyzed in either reducing (a final concentration of 2.5% beta-mercaptoethanol was added to denature the samples at 95° C. for 5 min), or non-reducing gradient SDS-PAGE gels (4-20%, Bio-Rad, Richmond, Calif., USA). The prestained broad range protein standard marker (7-175 kDa) run along with the protein samples in the SDS-PAGE gel was purchased from NEB. The reducing SDS-PAGE gels were visualized by Coomassie Blue staining. The fluorescent proteins in the non-reducing SDS-PAGE gels were visualized under a 488 nm laser with a 530 nm filter using a Bio-Rad Molecular Imager FX Pro.

Sequence Information

Target sequence (ZsGreen1, adapted from Clontech's pZsGreen1-C1 vector)

SEQ ID NO. 1
GGTCGCCACCATGGCCCAGTCCAAGCACGGCCTGACCAAGGAGATGACCATG

AAGTACCGCATGGAGGGCTGCGTGGACGGCCACAAGTTCGTGATCACCGGCG

AGGGCATCGGCTACCCCTTCAAGGGCAAGCAGGCCATCAACCTGTGCGTGGT

GGAGGGCGGCCCCTTGCCCTTCGCCGAGGACATCTTGTCCGCCGCCTTCATGT

ACGGCAACCGCGTGTTCACCGAGTACCCCCAGGACATCGTCGACTACTTCAA

GAACTCCTGCCCCGCCGGCTACACCTGGGACCGCTCCTTCCTGTTCGAGGACG

GCGCCGTGTGCATCTGCAACGCCGACATCACCGTGAGCGTGGAGGAGAACTG

CATGTACCACGAGTCCAAGTTCTACGGCGTGAACTTCCCCGCCGACGGCCCC

GTGATGAAGAAGATGACCGACAACTGGGAGCCCTCCTGCGAGAAGATCATCC

CCGTGCCCAAGCAGGGCATCTTGAAGGGCGACGTGAGCATGTACCTGCTGCT

GAAGGACGGTGGCCGCTTGCGCTGCCAGTTCGACACCGTGTACAAGGCCAAG

TCCGTGCCCCGCAAGATGCCCGACTGGCACTTCATCCAGCACAAGCTGACCC

GCGAGGACCGCAGCGACGCCAAGAACCAGAAGTGGCACCTGACCGAGCACG

CCATCGCCTCCGGCTCCGCCTTGCCCTGA

Note:
The underscored region is the Kozak sequence. The initial GG is
included in the T7 RNAP transcript for better transcription efficiency.

Target segment-RNAs for ZsGreen1 assembly (5' to 3')

| SEQ ID NO. 2 | 1 | GGUCGCCACCAUGGCCCAGUCCAAGCACGGCCUGACCAA |
| SEQ ID NO. 3 | 2 | GGAGAUGACCAUGAAGUACCGCAUGGAGGGCUGCGU |
| SEQ ID NO. 4 | 3 | GGACGGCCACAAGUUCGUGAUCACCGGCGA |
| SEQ ID NO. 5 | 4 | GGGCAUCGGCUACCCCUUCAAGGGCAAGCA |

-continued

| | | |
|---|---|---|
| SEQ ID NO. 6 | 5 | GGCCAUCAACCUGUGCGUGGUGGAGGGCGGCCCCUUGCCCUUCGCCGA |
| SEQ ID NO. 7 | 6 | GGACAUCUUGUCCGCCGCCUUCAUGUACGGCAACCGCGUGUUCACCGAGUACCCCCA |
| SEQ ID NO. 8 | 7 | GGACAUCGUCGACUACUUCAAGAACUCCUGCCCCGCC |
| SEQ ID NO. 9 | 8 | GGCUACACCUGGGACCGCUCCUUCCUGUUCGA |
| SEQ ID NO. 10 | 9 | GGACGGCGCCGUGUGCAUCUGCAACGCCGACAUCACCGUGAGCGU |
| SEQ ID NO. 11 | 10 | GGAGGAGAACUGCAUGUACCACGAGUCCAAGUUCUAC |
| SEQ ID NO. 12 | 11 | GGCGUGAACUUCCCCGCCGACGGCCCCGUGAUGAAGAAGAUGACCGACAACU |
| SEQ ID NO. 13 | 12 | GGGAGCCCUCCUGCGAGAAGAUCAUCCCCGUGCCCAAGCA |
| SEQ ID NO. 14 | 13 | GGGCAUCUUGAAGGGCGACGUGAGCAUGUACCUGCUGCUGAA |
| SEQ ID NO. 15 | 14 | GGACGGUGGCCGCUUGCGCUGCCAGUUCGACACCGUGUACAA |
| SEQ ID NO. 16 | 15 | GGCCAAGUCCGUGCCCCGCAAGAUGCCCGACU |
| SEQ ID NO. 17 | 16 | GGCACUUCAUCCAGCACAAGCUGACCCGCGA |
| SEQ ID NO. 18 | 17 | GGACCGCAGCGACGCCAAGAACCAGAAGUGGCACCUGACCGAGCACGCCAUCGCCUCC |
| SEQ ID NO. 19 | 18 | GGCUCCGCCUUGCCCUGA |

| Target splint-RNAs for ZsGreen1 assembly (5' to 3') | | |
|---|---|---|
| SEQ ID NO. 20 | 1 | GGGCACGGCCUGACCAAGGAGAUGACCAUGAA |
| SEQ ID NO. 21 | 2 | GGCAUGGAGGGCUGCGUGGACGGCCACAAGUU |
| SEQ ID NO. 22 | 3 | GGCGUGAUCACCGGCGAGGGCAUCGGCUACCC |
| SEQ ID NO. 23 | 4 | GGCUUCAAGGGCAAGCAGGCCAUCAACCUGUG |
| SEQ ID NO. 24 | 5 | GGCUUGCCCUUCGCCGAGGACAUCUUGUCCGC |
| SEQ ID NO. 25 | 6 | GGCACCGAGUACCCCCAGGACAUCGUCGACUA |
| SEQ ID NO. 26 | 7 | GGAACUCCUGCCCCGCCGGCUACACCUGGGAC |
| SEQ ID NO. 27 | 8 | GGCUCCUCCUGUUCGAGGACGGCGCCGUGUG |
| SEQ ID NO. 28 | 9 | GGCAUCACCGUGAGCGUGGAGGAGAACUGCAU |
| SEQ ID NO. 29 | 10 | GGGAGUCCAAGUUCUACGGCGUGAACUUCCCC |
| SEQ ID NO. 30 | 11 | GGAGAUGACCGACAACUGGGAGCCCUCCUGCG |
| SEQ ID NO. 31 | 12 | GGCCCCGUGCCCAAGCAGGGCAUCUUGAAGGG |
| SEQ ID NO. 32 | 13 | GGGUACCUGCUGCUGAAGGACGGUGGCCGCUU |
| SEQ ID NO. 33 | 14 | GGCGACACCGUGUACAAGGCCAAGUCCGUGCC |
| SEQ ID NO. 34 | 15 | GGGCAAGAUGCCCGACUGGCACUUCAUCCAGC |

-continued

| SEQ ID NO. 35 | 16 | GGCAAGCUGACCCGCGAGGACCGCAGCGACGC |
| SEQ ID NO. 36 | 17 | GGCACGCCAUCGCCUCCGGCUCCGCCUUGCCC |

RT-PCR primer sequences for cloning and sequencing:

SEQ ID NO. 37 ZsG-F: ATGGCCCAGTCCAAGCAC (Sigma Aldrich, MO, USA)

SEQ ID NO. 38 ZsG-R-w-6His: CTAGTGGTGATGGTGATGATGGGCAAGGCGGAGC (Sigma Aldrich, MO, USA)

RT-PCR primer sequences for amplification of T7 promoter appended ZsGreen1 gene:

SEQ ID NO. 39 T7P-ZsG-F: CAGTAATACGACTCACTATAGGTCGCCACCATGGCCCAGTCCAAGCACG (Sigma Aldrich, MO, USA)

SEQ ID NO. 40 ZsG-R: TCAGGGCAAGGCGGAGC (Sigma Aldrich, MO, USA)

Complementary sequence to T7 RNA polymerase promoter for in vitro RNA transcription:

SEQ ID NO. 41 FAM(6-carboxyfluorescein)-CAGTAATACGACTCACTATAGG ((Integrated DNA Technologies, IA, USA)

Sequences on the microarray (5'→3'):

| SEQ ID NO. | | Copy # | Sequences |
|---|---|---|---|
| 42 | 1 | 1 | CCACTGTTGCAAAGTTATACTCTTGCAGGTCATCGGCCTTTTTTTTTT (QC) |
| 43 | 2 | 1 | ACTCTTGCAGGTCA CGGCCCACTGTTGCAAAGTTATCCTTTTTTTTTT (QC) |
| 44 | 3 | 3 | TTGGTCAGGCCGTGCTTGGACTGGGCCATGGTGGCGACCTATAGTGAGTCGTATTACTGTTTTTTTTTT (seg) |
| 45 | 4 | 1 | ACGCAGCCCTCCATGCGGT CTTCATGGTCATCTCCTATAGTGAGTCGTATTACTGTTTTTTTTTT(seg) |
| 46 | 5 | 1 | TCGCCGGTGATCACGAACTTGTGGCCGTCCTATAGTGAGTCGTATTACTGTTTTTTTTTT(seg) |
| 47 | 6 | 1 | TGCTTGCCCTTGAAGGGGTAGCCGATGCCCTATAGTGAGTCGTATTACTGTTTTTTTTTT(seg) |
| 48 | 7 | 5 | TCGGCGAAGGGCAAGGGCCGCCCTCCACCACGCACAGGTTGATGGCCTATAGTGAGTCGTATTACTGTTTT TTTTTT(seg) |
| 49 | 8 | 5 | TGGGGGTACTCGGTGAACACGCGGTTGCCGTACATGAAGGCGGCGGACAAGATGTCCTATAGTGAGTCGTAT TACTGTTTTTTTTTT(seg) |
| 50 | 9 | 1 | GGCGGGGCAGGAGTTCTTGAAGTAGTCGACGATGTCCTATAGTGAGTCGTATTACTGTTTTTTTTTT(seg) |
| 51 | 10 | 1 | TCGAACAGGAAGGAGCGGTCCCAGGTGTAGCCTATAGTGAGTCGTATTACTGTTTTTTTTTT(seg) |
| 52 | 11 | 3 | ACGCTCACGGTGATGTCGGCGTTGCAGATGCACACGGCGCCGTCCTATAGTGAGTCGTATTACTGTTTTTTT TT(seg) |
| 53 | 12 | 2 | GTAGAACTTGGACTCGTGGTACATGCAGTTCTCCTCCTATAGTGAGTCGTATTACTGTTTTTTTTTT(seg) |
| 54 | 13 | 5 | AGTTGTCGGTCATCTTCTTCATCACGGGGCCGTCGGCGGGGAAGTTCACGCCTATAGTGAGTCGTATTACTGT TTTTTTTT(seg) |
| 55 | 14 | 3 | TGCTTGGGCACGGGGATGATCTTCTCGCAGGAGGGCTCCCTATAGTGAGTCGTATTACTGTTTTTTTTTT(seg) |
| 56 | 15 | 3 | TTCAGCAGCAGGTACATGCTCACGTCGCCCTTCAAGATGCCCTATAGTGAGTCGTATTACTGTTTTTTTTTT(seg) |
| 57 | 16 | 3 | TTGTACACGGTGTCGAACTGGCAGCGCAAGCGGCCACCGTCCTATAGTGAGTCGTATTACTGTTTTTTTTTT(seg) |
| 58 | 17 | 1 | AGTCGGGCATCTTGCGGGGCACGGACTTGGCCTATAGTGAGTCGTATTACTGTTTTTTTTTT(seg) |
| 59 | 18 | 1 | TCGCGGGTCAGCTTGTGCTGGATGAAGTGCCTATAGTGAGTCGTATTACTGTTTTTTTTTT(seg) |
| 60 | 19 | 5 | GGAGGCGATGGCGTGCTCGGTCAGGTGCCACTTCTGGTTCTTGGCGTCGCTGCGGTCCTATAGTGAGTCGTA TTACTGTTTTTTTTTT(seg) |
| 61 | 20 | 1 | TCAGGGCAAGGCGGAGCCTATAGTGAGTCGTATTACTGTTTTTTTTTT(seg) |
| 62 | 21 | 1 | GCACGGCCTGACCAAGGAGATGACCATGAACCTATAGTGAGTCGTATTACTGTTTTTTTTTT(splint) |
| 63 | 22 | 1 | CATGGAGGGCTGCGTGGACGGCCACAAGTTCCTATAGTGAGTCGTATTACTGTTTTTTTTTT(splint) |
| 64 | 23 | 1 | CGTGATCACCGGCGAGGGCATCGGCTACCCTATAGTGAGTCGTATTACTGTTTTTTTTTT(splint) |
| 65 | 24 | 1 | CTTCAAGGGCAAGCAGGCCATCAACCTGTGCCTATAGTGAGTCGTATTACTGTTTTTTTTTT(splint) |

| | | | |
|---|---|---|---|
| 66 | 25 | 1 | CTTGCCCTTCGCCGAGGACATCTTGTCCGCCTATAGTGAGTCGTATTACTGTTTTTTTTTT (splint) |
| 67 | 26 | 1 | CACCGAGTACCCCCAGGACATCGTCGACTACCTATAGTGAGTCGTATTACTGTTTTTTTTTT (splint) |
| 68 | 27 | 1 | AACTCCTGCCCCGCCGGCTACACCTGGGACCTATAGTGAGTCGTATTACTGTTTTTTTTTT (splint) |
| 69 | 28 | 1 | CTCCTTCCTGTTCGAGGACGGCGCCGTGTGCCTATAGTGAGTCGTATTACTGTTTTTTTTTT (splint) |
| 70 | 29 | 1 | CATCACCGTGAGCGTGGAGGAGAACTGCATCCTATAGTGAGTCGTATTACTGTTTTTTTTTT (splint) |
| 71 | 30 | 1 | GAGTCCAAGTTCTACGGCGTGAACTTCCCCTATAGTGAGTCGTATTACTGTTTTTTTTTT (splint) |
| 72 | 31 | 1 | AGATGACCGACAACTGGGAGCCCTCCTGCGCCTATAGTGAGTCGTATTACTGTTTTTTTTTT (splint) |
| 73 | 32 | 1 | CCCCGTGCCCAAGCAGGGCATCTTGAAGGGCCTATAGTGAGTCGTATTACTGTTTTTTTTTT (splint) |
| 74 | 33 | 1 | GTACCTGCTGCTGAAGGACGGTGGCCGCTTCCTATAGTGAGTCGTATTACTGTTTTTTTTTT (splint) |
| 75 | 34 | 1 | CGACACCGTGTACAAGGCCAAGTCCGTGCCTATAGTGAGTCGTATTACTGTTTTTTTTTT (splint) |
| 76 | 35 | 1 | GCAAGATGCCCGACTGGCACTTCATCCAGCCTATAGTGAGTCGTATTACTGTTTTTTTTTT (splint) |
| 77 | 36 | 1 | CAAGCTGACCCGCGAGGACCGCAGCGACGCCTATAGTGAGTCGTATTACTGTTTTTTTTTT (splint) |
| 78 | 37 | 1 | CACGCCATCGCCTCCGGCTCCGCCTTGCCCTATAGTGAGTCGTATTACTGTTTTTTTTTT (splint) |

Note:
3' tethered on the array surface. There are 18 segmented oligos, 17 splint oligos, and 2 quality control oligos. Multiple duplicate features were made as marked. Each feature is sized 1680 µm x 1232 µm.

Alignment of Sanger Sequencing Data of ZsGreen1 Assemblies

ZsGreen1 gene assemblies from DNA arrays fabricated on either amorphous carbon surfaces (sequence #1 to #25) or on silanized glass surfaces (sequence #26 to #51) were Sanger sequenced (Functional Biosciences, Inc., WI, USA) and aligned with the ZsGreen1 target sequence (see FIG. 4A-L). It should be noted sequenced nucleotides #1 to #18 correspond to the forward primer sequence (ZsG-F), and sequenced nucleotides #680 to #714 correspond to the reverse primer sequence (ZsG-R-w-6His) for ZsGreen1 RT-PCR amplification. Excluding the primer regions, 16,525 assembled nucleotides from the DNA array fabricated on the amorphous carbon surface were analyzed and 25 transitions, 3 transversions, 1 deletion, and no insertions were identified, which corresponds to an error rate of 0.1755%; whereas 17,186 assembled nucleotides from the DNA array on the silanized glass surface were analyzed and 24 transitions, no transversion, 1 deletion, and 1 insertion were identified, which corresponds to an error rate of 0.1513%. This sequence analysis of cloned constructs indicated a yield of correct constructs of approximately 40%.

Analyzing the primer sequences (character bordered), which were conventionally column synthesized from Sigma Aldrich, 1 transitions, 2 transversions, 3 deletions, and 2 insertions were identified in the ZsG-R-w-6His primer region (35 nt long; 1,785 nucleotides were analyzed; corresponds to an error rate of 0.448%) whereas no errors were found in the short ZsG-F primer region (18 nt long).

Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference. It is understood that the invention is not confined to the specific reagents, formulations, reaction conditions, etc., herein illustrated and described, but embraces such modified forms thereof as come within the scope of the following claims.

REFERENCES

1. Nilsson, B. L., Soellner, M. B. and Raines, R. T. (2005) Chemical synthesis of proteins. *Annu. Rev. Biophys. Biomolec. Struct.*, 34, 91-118.
2. Itakura, K., Hirose, T., Crea, R., Riggs, A. D., Heyneker, H. L., Bolivar, F. and Boyer, H. W. (1977) Expression in *Escherichia coli* of a chemically synthesized gene for the hormone somatostatin. *Science*, 198, 1056-1063.
3. Stemmer, W. P., Crameri, A., Ha, K. D., Brennan, T. M. and Heyneker, H. L. (1995) Single-step assembly of a gene and entire plasmid from large numbers of oligodeoxyribonucleotides. *Gene*, 164, 49-53.
4. Richmond, K. E., Li, M. H., Rodesch, M. J., Patel, M., Lowe, A. M., Kim, C., Chu, L. L., Venkataramaian, N., Flickinger, S. F., Kaysen, J. et al. (2004) Amplification and assembly of chip-eluted DNA (AACED): a method for high-throughput gene synthesis. *Nucleic Acids Res*, 32, 5011-5018.
5. Quan, J. Y., Saaem, I., Tang, N., Ma, S. M., Negre, N., Gong, H., White, K. P. and Tian, J. D. (2011) Parallel on-chip gene synthesis and application to optimization of protein expression. *Nat. Biotechnol.*, 29, 449-U239.
6. Matzas, M., Stahler, P. F., Kefer, N., Siebelt, N., Boisguerin, V., Leonard, J. T., Keller, A., Stahler, C. F., Haberle, P., Gharizadeh, B. et al. (2010) High-fidelity gene synthesis by retrieval of sequence-verified DNA identified using high-throughput pyrosequencing. *Nat. Biotechnol.*, 28, 1291-U1101.
7. Kosuri, S., Eroshenko, N., LeProust, E. M., Super, M., Way, J., Li, J. B. and Church, G. M. (2010) Scalable gene synthesis by selective amplification of DNA pools from high-fidelity microchips. *Nat. Biotechnol.*, 28, 1295-U1108.
8. Borovkov, A. Y., Loskutov, A. V., Robida, M. D., Day, K. M., Cano, J. A., Le Olson, T., Patel, H., Brown, K., Hunter, P. D. and Sykes, K. F. (2010) High-quality gene assembly directly from unpurified mixtures of microarray-synthesized oligonucleotides. *Nucleic Acids Res*, 38, e180.

9. Kim, C., Kaysen, J., Richmond, K., Rodesch, M., Binkowski, B., Chu, L., Li, M., Heinrich, K., Blair, S., Belshaw, P. et al. (2006) Progress in gene assembly from a MAS-driven DNA microarray. *Microelectron. Eng.*, 83, 1613-1616.

10. Tian, J. D., Gong, H., Sheng, N. J., Zhou, X. C., Gulari, E., Gao, X. L. and Church, G. (2004) Accurate multiplex gene synthesis from programmable DNA microchips. *Nature*, 432, 1050-1054.

11. Xiong, A. S., Yao, Q. H., Peng, R. H., Li, X., Fan, H. Q., Cheng, Z. M. and Li, Y. (2004) A simple, rapid, high-fidelity and cost-effective PCR-based two-step DNA synthesis method for long gene sequences. *Nucleic Acids Res*, 32, e98.

12. Xiong, A. S., Peng, R. H., Zhuang, J., Liu, J. G., Gao, F., Chen, J. M., Cheng, Z. M. and Yao, Q. H. (2008) Non-polymerase-cycling-assembly-based chemical gene synthesis: strategies, methods, and progress. *Biotechnol. Adv.*, 26, 121-134.

13. Kozak, M. (1987) An analysis of 5'-noncoding sequences from 699 vertebrate messenger RNAs. *Nucleic Acids Res*, 15, 8125-8148.

14. Milligan, J. F., Groebe, D. R., Witherell, G. W. and Uhlenbeck, O. C. (1987) Oligoribonucleotide Synthesis Using T7 Rna-Polymerase and Synthetic DNA Templates. *Nucleic Acids Res*, 15, 8783-8798.

15. Martin, C. T., Muller, D. K. and Coleman, J. E. (1988) Processivity in early stages of transcription by T7 RNA polymerase. *Biochemistry*, 27, 3966-3974.

16. Guo, Z., Guilfoyle, R. A., Thiel, A. J., Wang, R. F. and Smith, L. M. (1994) Direct fluorescence analysis of genetic polymorphisms by hybridization with oligonucleotide arrays on glass supports. *Nucleic Acids Res*, 22, 5456-5465.

17. Singh-Gasson, S., Green, R. D., Yue, Y. J., Nelson, C., Blattner, F., Sussman, M. R. and Cerrina, F. (1999) Maskless fabrication of light-directed oligonucleotide microarrays using a digital micromirror array. *Nat. Biotechnol.*, 17, 974-978.

18. Phillips, M. F., Lockett, M. R., Rodesch, M. J., Shortreed, M. R., Cerrina, F. and Smith, L. M. (2008) In situ oligonucleotide synthesis on carbon materials: stable substrates for microarray fabrication. *Nucleic Acids Res*, 36, e7.

19. Lockett, M. R. and Smith, L. M. (2009) Fabrication and characterization of DNA arrays prepared on carbon-on-metal substrates. *Anal Chem*, 81, 6429-6437.

20. Lockett, M. R., Weibel, S. C., Phillips, M. F., Shortreed, M. R., Sun, B., Corn, R. M., Hamers, R. J., Cerrina, F. and Smith, L. M. (2008) Carbon-on-metal films for surface plasmon resonance detection of DNA arrays. *Journal of the American Chemical Society*, 130, 8611-8613.

21. Milligan, J. F. and Uhlenbeck, O. C. (1989) Synthesis of small RNAs using T7 RNA polymerase. *Methods in Enzymology*, 180, 51-62.

22. Hochuli, E., Bannwarth, W., Dobeli, H., Gentz, R. and Stuber, D. (1988) Genetic approach to facilitate purification of recombinant proteins with a novel metal chelate adsorbent. *Bio-Technol*, 6, 1321-1325.

23. Cleary, M. A., Kilian, K., Wang, Y. Q., Bradshaw, J., Cavet, G., Ge, W., Kulkarni, A., Paddison, P. J., Chang, K., Sheth, N. et al. (2004) Production of complex nucleic acid libraries using highly parallel in situ oligonucleotide synthesis. *Nat. Methods*, 1, 241-248.

24. Gao, X., Gaffney, B. L., Senior, M., Riddle, R. R. and Jones, R. A. (1985) Methylation of thymine residues during oligonucleotide synthesis. *Nucleic Acids Res*, 13, 573-584.

25. Pon, R. T., Damha, M. J. and Ogilvie, K. K. (1985) Modification of guanine bases by nucleoside phosphoramidite reagents during the solid phase synthesis of oligonucleotides. *Nucleic Acids Res*, 13, 6447-6465.

26. Pon, R. T., Usman, N., Damha, M. J. and Ogilvie, K. K. (1986) PREVENTION OF GUANINE MODIFICATION AND CHAIN CLEAVAGE DURING THE SOLID-PHASE SYNTHESIS OF OLIGONUCLEOTIDES USING PHOSPHORAMIDITE DERIVATIVES. *Nucleic Acids Res*, 14, 6453-6470.

27. Crippa, S., Digennaro, P., Lucini, R., Orlandi, M. and Rindone, B. (1993) CHARACTERIZATION OF ADDUCTS OF NUCLEIC BASES AND ACRYLIC-MONOMERS. *Gazzetta Chimica Italiana*, 123, 197-203.

28. Prime, K. L. and Whitesides, G. M. (1993) Adsorption of Proteins onto Surfaces Containing End-Attached Oligo (Ethylene Oxide)—a Model System Using Self-Assembled Monolayers. *Journal of the American Chemical Society*, 115, 10714-10721.

29. Pease, A. C., Solas, D., Sullivan, E. J., Cronin, M. T., Holmes, C. P. and Fodor, S. P. A. (1994) Light-Generated Oligonucleotide Arrays for Rapid DNA-Sequence Analysis. *P Natl Acad Sci USA*, 91, 5022-5026.

30. McGall, G. H., Barone, A. D., Diggelmann, M., Fodor, S. P. A., Gentalen, E. and Ngo, N. (1997) The efficiency of light-directed synthesis of DNA arrays on glass substrates. *J Am Chem Soc*, 119, 5081-5090.

31. Walbert, S., Pfleiderer, W. and Steiner, U. E. (2001) Photolabile protecting groups for nucleosides: Mechanistic studies of the 2-(2-nitrophenyl)ethyl group. *Helvetica Chimica Acta*, 84, 1601-1611.

What is claimed is:

1. An oligonucleotide array for RNA-mediated assembly of a target RNA molecule, comprising:
   (a) a plurality of first surface-bound oligonucleotides each having a segment sequence corresponding to a portion of a target RNA and a complementary RNAP promoter sequence operably-linked to said segment sequence's 3' termini, wherein two or more of the segment sequences correspond to different portions of the target RNA; and
   (b) a plurality of second surface-bound oligonucleotides each having a splint sequence corresponding to a portion of the target RNA that complements and partially overlaps at least two of the two or more segment sequences of the first surface-bound oligonucleotides corresponding to different portions of the target RNA, said second surface-bound oligonucleotides including an RNAP promoter sequence operably-linked to their splint sequence's 3' termini,
   wherein said first and second surface-bound oligonucleotides are linked at their 3' termini to a surface of the oligonucleotide array.

2. The oligonucleotide array according to claim 1, wherein the 5' end of each segment sequence and each splint sequence corresponds to a GG dinucleotide in the target RNA molecule.

3. The oligonucleotide array according to claim 1, wherein the target RNA molecule is a full-length RNA transcript of a gene.

4. The oligonucleotide array according to claim 1, wherein the oligonucleotide array's surface comprises a silanized glass or amorphous carbon deposited on a gold film.

5. The oligonucleotide array according to claim 1, wherein said surface-bound oligonucleotides include a spacer, a T7 RNAP promoter sequence, a CC dinucleotide and either the segment sequence or the splint sequence.

6. The oligonucleotide array according to claim 1, wherein oligonucleotide array further comprises a third oligonucleotide encoding an RNAP promoter sequence to the complementary RNAP promoter sequence of the first and second surface-bound oligonucleotides to yield double-stranded RNAP promoters.

* * * * *

SEQUENCE LISTING

<160> NUMBER OF SEQ ID NOS: 82

<210> SEQ ID NO 1
<211> LENGTH: 706
<212> TYPE: DNA
<213> ORGANISM: Artificial Sequence
<220> FEATURE:
<223> OTHER INFORMATION: Target sequence (ZsGreen1, adapted from Clontech's pZsGreen1-C1 vector)

<400> SEQUENCE: 1

```
ggtcgccacc atggcccagt ccaagcacgg cctgaccaag gagatgacca tgaagtaccg      60
```

```
catggagggc tgcgtggacg gccacaagtt cgtgatcacc ggcgagggca tcggctaccc    120
cttcaagggc aagcaggcca tcaacctgtg cgtggtggag ggcggcccct tgcccttcgc    180
cgaggacatc ttgtccgccg ccttcatgta cggcaaccgc gtgttcaccg agtacccca     240 ggacatcgtc gactacttca gaactcctg ccccgccggc tacacctggg accgctcctt    300
cctgttcgag gacggcgccg tgtgcatctg caacgccgac atcaccgtga gcgtggagga    360
gaactgcatg taccacgagt ccaagttcta cggcgtgaac ttccccgccg acggccccgt    420
gatgaagaag atgaccgaca ctgggagcc tcctgcgag aagatcatcc ccgtgcccaa    480
gcagggcatc ttgaagggcg acgtgagcat gtacctgctg ctgaaggacg gtggccgctt    540
gcgctgccag ttcgacaccg tgtacaaggc caagtccgtg ccccgcaaga tgcccgactg    600
gcacttcatc cagcacaagc tgacccgcga ggaccgcagc gacgccaaga accagaagtg    660
gcacctgacc gagcacgcca tcgcctccgg ctccgccttg ccctga                  706
```

```
<210> SEQ ID NO 2
<211> LENGTH: 39
<212> TYPE: RNA
<213> ORGANISM: Artificial Sequence
<220> FEATURE:
<223> OTHER INFORMATION: #1 Target segment RNAs for ZsGreen1 assembly
      (5' to 3')

<400> SEQUENCE: 2 gucgccacc auggcccagu ccaagcacgg ccugaccaa                             39

<210> SEQ ID NO 3
<211> LENGTH: 36
<212> TYPE: RNA
<213> ORGANISM: Artificial Sequence
<220> FEATURE:
<223> OTHER INFORMATION: #2 Target segment-RNAs for ZsGreen1 assembly
      (5' to 3')

<400> SEQUENCE: 3
ggagaugacc augaaguacc gcauggaggg cugcgu                               36

<210> SEQ ID NO 4
<211> LENGTH: 30
<212> TYPE: RNA
<213> ORGANISM: Artificial Sequence
<220> FEATURE:
<223> OTHER INFORMATION: #3 Target segment-RNAs for ZsGreen1 assembly
      (5' to 3')

<400> SEQUENCE: 4
ggacggccac aaguucguga ucaccggcga                                      30

<210> SEQ ID NO 5
<211> LENGTH: 30
<212> TYPE: RNA
<213> ORGANISM: Artificial Sequence
<220> FEATURE:
<223> OTHER INFORMATION: #4 Target segment-RNAs for ZsGreen1 assembly
      (5' to 3')

<400> SEQUENCE: 5
gggcaucggc uaccccuuca agggcaagca                                      30

<210> SEQ ID NO 6
<211> LENGTH: 48
<212> TYPE: RNA
```

<213> ORGANISM: Artificial Sequence
<220> FEATURE:
<223> OTHER INFORMATION: #5 Target segment-RNAs for ZsGreen1 assembly
      (5' to 3')

<400> SEQUENCE: 6
ggccaucaac cugugcgugg uggagggcgg ccccuugccc uucgccga                48

<210> SEQ ID NO 7
<211> LENGTH: 57
<212> TYPE: RNA
<213> ORGANISM: Artificial Sequence
<220> FEATURE:
<223> OTHER INFORMATION: #6 Target segment-RNAs for ZsGreen1 assembly
      (5' to 3')

<400> SEQUENCE: 7
ggacaucuug uccgccgccu ucauguacgg caaccgcgug uucaccgagu accccca      57

<210> SEQ ID NO 8
<211> LENGTH: 37
<212> TYPE: RNA
<213> ORGANISM: Artificial Sequence
<220> FEATURE:
<223> OTHER INFORMATION: #7 Target segment-RNAs for ZsGreen1 assembly
      (5' to 3')

<400> SEQUENCE: 8
ggacaucguc gacuacuuca agaacuccug ccccgcc                37

<210> SEQ ID NO 9
<211> LENGTH: 32
<212> TYPE: RNA
<213> ORGANISM: Artificial Sequence
<220> FEATURE:
<223> OTHER INFORMATION: #8 Target segment-RNAs for ZsGreen1 assembly
      (5' to 3')

<400> SEQUENCE: 9
ggcuacaccu gggaccgcuc cuuccuguuc ga                32

<210> SEQ ID NO 10
<211> LENGTH: 45
<212> TYPE: RNA
<213> ORGANISM: Artificial Sequence
<220> FEATURE:
<223> OTHER INFORMATION: #9 Target segment-RNAs for ZsGreen1 assembly
      (5' to 3')

<400> SEQUENCE: 10
ggacggcgcc gugugcaucu gcaacgccga caucaccgug agcgu                45

<210> SEQ ID NO 11
<211> LENGTH: 37
<212> TYPE: RNA
<213> ORGANISM: Artificial Sequence
<220> FEATURE:
<223> OTHER INFORMATION: #10 Target segment-RNAs for ZsGreen1 assembly
      (5' to 3')

<400> SEQUENCE: 11
ggaggagaac ugcauguacc acgaguccaa guucuac                37

<210> SEQ ID NO 12
<211> LENGTH: 52
<212> TYPE: RNA
<213> ORGANISM: Artificial Sequence -continued

```
<220> FEATURE:
<223> OTHER INFORMATION: #11 Target segment-RNAs for Zg=sGreen1 assembly
      (5' to 3')

<400> SEQUENCE: 12
ggcgugaacu ucccgccga cggccccgug augaagaaga ugaccgacaa cu          52

<210> SEQ ID NO 13
<211> LENGTH: 40
<212> TYPE: RNA
<213> ORGANISM: Artificial Sequence
<220> FEATURE:
<223> OTHER INFORMATION: #12 Target segment-RNAs for ZsGreen1 assembly
      (5' to 3')

<400> SEQUENCE: 13
gggagcccuc cugcgagaag aucauccccg ugcccaagca                       40

<210> SEQ ID NO 14
<211> LENGTH: 42
<212> TYPE: RNA
<213> ORGANISM: Artificial Sequence
<220> FEATURE:
<223> OTHER INFORMATION: #13 Target segment-RNAs for ZsGreen1 assembly
      (5' to 3')

<400> SEQUENCE: 14
gggcaucuug aagggcgacg ugagcaugua ccugcugcug aa                    42

<210> SEQ ID NO 15
<211> LENGTH: 42
<212> TYPE: RNA
<213> ORGANISM: Artificial Sequence
<220> FEATURE:
<223> OTHER INFORMATION: #14 Target segment-RNAs for ZsGreen1 assembly
      (5' to 3')

<400> SEQUENCE: 15
ggacggyggc cgcuugcgcu gccaguucga caccguguac aa                    42

<210> SEQ ID NO 16
<211> LENGTH: 32
<212> TYPE: RNA
<213> ORGANISM: Artificial Sequence
<220> FEATURE:
<223> OTHER INFORMATION: #15 Target segment-RNAs for AsGreen1 assembly
      (5' to 3')

<400> SEQUENCE: 16
ggccaagucc gugccccgca agaugcccga cu                               32

<210> SEQ ID NO 17
<211> LENGTH: 31
<212> TYPE: RNA
<213> ORGANISM: Artificial Sequence
<220> FEATURE:
<223> OTHER INFORMATION: #16 Target segment-RNAs for ZsGreen1 assembly
      (5' to 3')

<400> SEQUENCE: 17
ggcacuucau ccagcacaag cugacccgcg a                                31

<210> SEQ ID NO 18
<211> LENGTH: 58
<212> TYPE: RNA
<213> ORGANISM: Artificial Sequence
<220> FEATURE:
```

```
<223> OTHER INFORMATION: #17 Target segment-RNAs for ZsGreen1 assembly
      (5' to 3')

<400> SEQUENCE: 18
ggaccgcagc gacgccaaga accagaagug gcaccugacc gagcacgcca ucgccucc        58

<210> SEQ ID NO 19
<211> LENGTH: 18
<212> TYPE: RNA
<213> ORGANISM: Artificial Sequence
<220> FEATURE:
<223> OTHER INFORMATION: #18 Target segment-RNAs for ZsGreen1 assembly
      (5' to 3')

<400> SEQUENCE: 19
ggcuccgccu ugcccuga                                                    18

<210> SEQ ID NO 20
<211> LENGTH: 32
<212> TYPE: RNA
<213> ORGANISM: Artificial Sequence
<220> FEATURE:
<223> OTHER INFORMATION: #1 Target splint-RNAs for ZsGreen1 assembly
      (5' to 3')

<400> SEQUENCE: 20
gggcacggcc ugaccaagga gaugaccaug aa                                    32

<210> SEQ ID NO 21
<211> LENGTH: 32
<212> TYPE: RNA
<213> ORGANISM: Artificial Sequence
<220> FEATURE:
<223> OTHER INFORMATION: #2 Target splint-RNAs for ZsGreen1 assembly
      (5' to 3')

<400> SEQUENCE: 21
ggcauggagg gcugcgugga cggccacaag uu                                    32

<210> SEQ ID NO 22
<211> LENGTH: 32
<212> TYPE: RNA
<213> ORGANISM: Artificial Sequence
<220> FEATURE:
<223> OTHER INFORMATION: #3 Target splint-RNAs for ZsGreen1 assembly
      (5' to 3')

<400> SEQUENCE: 22
ggcgugauca ccggcgaggg caucggcuac cc                                    32

<210> SEQ ID NO 23
<211> LENGTH: 32
<212> TYPE: RNA
<213> ORGANISM: Artificial Sequence
<220> FEATURE:
<223> OTHER INFORMATION: #4 Target splint-RNAs for ZsGreen1 assembly
      (5' to 3')

<400> SEQUENCE: 23
ggcuucaagg gcaagcaggc caucaaccug ug                                    32

<210> SEQ ID NO 24
<211> LENGTH: 32
<212> TYPE: RNA
<213> ORGANISM: Artificial Sequence
<220> FEATURE:
<223> OTHER INFORMATION: #5 Target splint-RNAs for ZsGreen1 assembly
```

-continued (5' to 3')

<400> SEQUENCE: 24
ggcuugcccu ucgccgagga caucuugucc gc          32

<210> SEQ ID NO 25
<211> LENGTH: 32
<212> TYPE: RNA
<213> ORGANISM: Artificial Sequence
<220> FEATURE:
<223> OTHER INFORMATION: #6 Target splint-RNAs for ZsGreen1 assembly
      (5' to 3')

<400> SEQUENCE: 25
ggcaccgagu accccagga caucgucgac ua          32

<210> SEQ ID NO 26
<211> LENGTH: 32
<212> TYPE: RNA
<213> ORGANISM: Artificial Sequence
<220> FEATURE:
<223> OTHER INFORMATION: #7 Target splint-RNAs for ZsGreen1 assembly
      (5' to 3')

<400> SEQUENCE: 26
ggaacuccug ccccgccggc uacaccuggg ac          32

<210> SEQ ID NO 27
<211> LENGTH: 32
<212> TYPE: RNA
<213> ORGANISM: Artificial Sequence
<220> FEATURE:
<223> OTHER INFORMATION: #8 Target splint-RNAs for ZsGreen1 assembly
      (5' to 3')

<400> SEQUENCE: 27
ggcuccuucc uguucgagga cggcgccgug ug          32

<210> SEQ ID NO 28
<211> LENGTH: 32
<212> TYPE: RNA
<213> ORGANISM: Artificial Sequence
<220> FEATURE:
<223> OTHER INFORMATION: #9 Target splint-RNAs for ZsGreen1 assembly
      (5' to 3')

<400> SEQUENCE: 28
ggcaucaccg ugagcgugga ggagaacugc au          32

<210> SEQ ID NO 29
<211> LENGTH: 32
<212> TYPE: RNA
<213> ORGANISM: Artificial Sequence
<220> FEATURE:
<223> OTHER INFORMATION: #10 Target splint-RNAs for ZsGreen1 assembly
      (5' to 3')

<400> SEQUENCE: 29
gggaguccaa guucuacggc gugaacuucc cc          32

<210> SEQ ID NO 30
<211> LENGTH: 32
<212> TYPE: RNA
<213> ORGANISM: Artificial Sequence
<220> FEATURE:
<223> OTHER INFORMATION: #11 Target splint-RNAs for ZsGreen1 assembly
      (5' to 3')

```
<400> SEQUENCE: 30
ggagaugacc gacaacuggg agcccuccug cg                                      32

<210> SEQ ID NO 31
<211> LENGTH: 32
<212> TYPE: RNA
<213> ORGANISM: Artificial Sequence
<220> FEATURE:
<223> OTHER INFORMATION: #12 Target splint-RNAs for ZsGreen1 assembly
      (5' to 3')

<400> SEQUENCE: 31
ggccccgugc ccaagcaggg caucuugaag gg                                      32

<210> SEQ ID NO 32
<211> LENGTH: 32
<212> TYPE: RNA
<213> ORGANISM: Artificial Sequence
<220> FEATURE:
<223> OTHER INFORMATION: #13 Target splint-RNAs for ZsGreen1 assembly
      (5' to 3')

<400> SEQUENCE: 32
ggguaccugc ugcugaagga cgguggccgc uu                                      32

<210> SEQ ID NO 33
<211> LENGTH: 32
<212> TYPE: RNA
<213> ORGANISM: Artificial Sequence
<220> FEATURE:
<223> OTHER INFORMATION: #14 Target splint-RNAs for ZsGreen1 assembly
      (5' to 3')

<400> SEQUENCE: 33
ggcgacaccg uguacaaggc caaguccgug cc                                      32

<210> SEQ ID NO 34
<211> LENGTH: 32
<212> TYPE: RNA
<213> ORGANISM: Artificial Sequence
<220> FEATURE:
<223> OTHER INFORMATION: #15 Target splint-RNAs for ZsGreen1 assembly
      (5' to 3')

<400> SEQUENCE: 34
gggcaagaug cccgacuggc acuucaucca gc                                      32

<210> SEQ ID NO 35
<211> LENGTH: 32
<212> TYPE: RNA
<213> ORGANISM: Artificial Sequence
<220> FEATURE:
<223> OTHER INFORMATION: #16 Target splint-RNAs for ZsGreen1 assembly
      (5' to 3')

<400> SEQUENCE: 35
ggcaagcuga cccgcgagga ccgcagcgac gc                                      32

<210> SEQ ID NO 36
<211> LENGTH: 32
<212> TYPE: RNA
<213> ORGANISM: Artificial Sequence
<220> FEATURE:
<223> OTHER INFORMATION: #17 Target splint-RNAs for ZsGreen1 assembly
      (5' to 3')
```

```
<400> SEQUENCE: 36
ggcacgccau cgccuccggc uccgccuugc cc                                    32

<210> SEQ ID NO 37
<211> LENGTH: 18
<212> TYPE: DNA
<213> ORGANISM: Artificial Sequence
<220> FEATURE:
<223> OTHER INFORMATION: ZsG-F RT-PCR primer

<400> SEQUENCE: 37
atggcccagt ccaagcac                                                    18

<210> SEQ ID NO 38
<211> LENGTH: 35
<212> TYPE: DNA
<213> ORGANISM: Artificial Sequence
<220> FEATURE:
<223> OTHER INFORMATION: ZsG-R-w-6His RT-PCR Primer

<400> SEQUENCE: 38
ctagtggtga tggtgatgat ggggcaaggc ggagc                                 35

<210> SEQ ID NO 39
<211> LENGTH: 49
<212> TYPE: DNA
<213> ORGANISM: Artificial Sequence
<220> FEATURE:
<223> OTHER INFORMATION: T7P-ZsG-F RT-PCR primer

<400> SEQUENCE: 39
cagtaatacg actcactata ggtcgccacc atggcccagt ccaagcacg                  49

<210> SEQ ID NO 40
<211> LENGTH: 17
<212> TYPE: DNA
<213> ORGANISM: Artificial Sequence
<220> FEATURE:
<223> OTHER INFORMATION: ZsG-R RT-PCR primer

<400> SEQUENCE: 40
tcagggcaag gcggagc                                                     17

<210> SEQ ID NO 41
<211> LENGTH: 22
<212> TYPE: DNA
<213> ORGANISM: Artificial Sequence
<220> FEATURE:
<223> OTHER INFORMATION: FAM(6-carboxyfluorescein) RT-PCR primer

<400> SEQUENCE: 41
cagtaatacg actcactata gg                                               22

<210> SEQ ID NO 42
<211> LENGTH: 48
<212> TYPE: DNA
<213> ORGANISM: Artificial Sequence
<220> FEATURE:
<223> OTHER INFORMATION: #1 Sequences on the microarray (5' to 3')

<400> SEQUENCE: 42
ccactgttgc aaagttatac tcttgcaggt catcggcctt ttttttt                    48

<210> SEQ ID NO 43
<211> LENGTH: 48
```

```
<212> TYPE: DNA
<213> ORGANISM: Artificial Sequence
<220> FEATURE:
<223> OTHER INFORMATION: #2 Sequences on the microarray (5' to 3')

<400> SEQUENCE: 43
actcttgcag gtcacggccc actgttgcaa agttatcctt tttttttt                    48

<210> SEQ ID NO 44
<211> LENGTH: 69
<212> TYPE: DNA
<213> ORGANISM: Artificial Sequence
<220> FEATURE:
<223> OTHER INFORMATION: #3 Sequences on the microarray (5' to 3')

<400> SEQUENCE: 44
ttggtcaggc cgtgcttgga ctgggccatg gtggcgacct atagtgagtc gtattactgt       60
tttttttt                                                                69

<210> SEQ ID NO 45
<211> LENGTH: 65
<212> TYPE: DNA
<213> ORGANISM: Artificial Sequence
<220> FEATURE:
<223> OTHER INFORMATION: #4 Sequences on the microarray (5' to 3')

<400> SEQUENCE: 45
acgcagccct ccatgcggtc ttcatggtca tctcctatag tgagtcgtat tactgttttt       60
ttttt                                                                   65

<210> SEQ ID NO 46
<211> LENGTH: 60
<212> TYPE: DNA
<213> ORGANISM: Artificial Sequence
<220> FEATURE:
<223> OTHER INFORMATION: #5 Sequences on the microarray (5' to 3')

<400> SEQUENCE: 46
tcgccggtga tcacgaactt gtggccgtcc tatagtgagt cgtattactg tttttttttt       60

<210> SEQ ID NO 47
<211> LENGTH: 60
<212> TYPE: DNA
<213> ORGANISM: Artificial Sequence
<220> FEATURE:
<223> OTHER INFORMATION: #6 Sequences on the microarray (5' to 3')

<400> SEQUENCE: 47
tgcttgccct tgaaggggta gccgatgccc tatagtgagt cgtattactg tttttttttt       60

<210> SEQ ID NO 48
<211> LENGTH: 78
<212> TYPE: DNA
<213> ORGANISM: Artificial Sequence
<220> FEATURE:
<223> OTHER INFORMATION: #7 Sequences on the microarray (5' to 3')

<400> SEQUENCE: 48
tcggcgaagg gcaagggggcc gccctccacc acgcacaggt tgatggccta tagtgagtcg      60
tattactgtt tttttttt                                                     78

<210> SEQ ID NO 49
<211> LENGTH: 87
<212> TYPE: DNA
```

```
<213> ORGANISM: Artificial Sequence
<220> FEATURE:
<223> OTHER INFORMATION: #8 Sequences on the microarray

<400> SEQUENCE: 49
tgggggtact cggtgaacac gcggttgccg tacatgaagg cggcggacaa gatgtcctat      60
agtgagtcgt attactgttt tttttt                                          87

<210> SEQ ID NO 50
<211> LENGTH: 67
<212> TYPE: DNA
<213> ORGANISM: Artificial Sequence
<220> FEATURE:
<223> OTHER INFORMATION: #9 Sequences on the microarray (5' to 3')

<400> SEQUENCE: 50
ggcggggcag gagttcttga agtagtcgac gatgtcctat agtgagtcgt attactgttt      60
tttttt                                                                67

<210> SEQ ID NO 51
<211> LENGTH: 62
<212> TYPE: DNA
<213> ORGANISM: Artificial Sequence
<220> FEATURE:
<223> OTHER INFORMATION: #10 Sequences on the microarray (5' to 3')

<400> SEQUENCE: 51
tcgaacagga aggagcggtc ccaggtgtag cctatagtga gtcgtattac tgttttttt      60 tt                                                                    62

<210> SEQ ID NO 52
<211> LENGTH: 75
<212> TYPE: DNA
<213> ORGANISM: Artificial Sequence
<220> FEATURE:
<223> OTHER INFORMATION: #11 Sequences on the microarray (5' to 3')

<400> SEQUENCE: 52
acgctcacgg tgatgtcggc gttgcagatg cacacggcgc cgtcctatag tgagtcgtat      60
tactgttttt ttttt                                                      75

<210> SEQ ID NO 53
<211> LENGTH: 67
<212> TYPE: DNA
<213> ORGANISM: Artificial Sequence
<220> FEATURE:
<223> OTHER INFORMATION: #12 Sequences on the microarray (5' to 3')

<400> SEQUENCE: 53
gtagaacttg gactcgtggt acatgcagtt ctcctcctat agtgagtcgt attactgttt      60
tttttt                                                                67

<210> SEQ ID NO 54
<211> LENGTH: 82
<212> TYPE: DNA
<213> ORGANISM: Artificial Sequence
<220> FEATURE:
<223> OTHER INFORMATION: #13 Sequences on the microarray

<400> SEQUENCE: 54
agttgtcggt catcttcttc atcacggggc cgtcggcggg gaagttcacg cctatagtga      60
gtcgtattac tgttttttttt tt                                             82
```

<210> SEQ ID NO 55
<211> LENGTH: 70
<212> TYPE: DNA
<213> ORGANISM: Artificial Sequence
<220> FEATURE:
<223> OTHER INFORMATION: #14 Sequences on the microarray (5' to 3')

<400> SEQUENCE: 55
tgcttgggca cggggatgat cttctcgcag gagggctccc tatagtgagt cgtattactg    60
tttttttttt                                                          70

<210> SEQ ID NO 56
<211> LENGTH: 72
<212> TYPE: DNA
<213> ORGANISM: Artificial Sequence
<220> FEATURE:
<223> OTHER INFORMATION: #15 Sequences on the microarray

<400> SEQUENCE: 56
ttcagcagca ggtacatgct cacgtcgccc ttcaagatgc cctatagtga gtcgtattac    60
tgtttttttt tt                                                       72

<210> SEQ ID NO 57
<211> LENGTH: 72
<212> TYPE: DNA
<213> ORGANISM: Artificial Sequence
<220> FEATURE:
<223> OTHER INFORMATION: #16 sequences on the microarray (5' to 3')

<400> SEQUENCE: 57
ttgtacacgg tgtcgaactg gcagcgcaag cggccaccgt cctatagtga gtcgtattac    60
tgtttttttt tt                                                       72

<210> SEQ ID NO 58
<211> LENGTH: 62
<212> TYPE: DNA
<213> ORGANISM: Artificial Sequence
<220> FEATURE:
<223> OTHER INFORMATION: #17 Sequences on the microarray (5' to 3')

<400> SEQUENCE: 58
agtcgggcat cttgcggggc acggacttgg cctatagtga gtcgtattac tgtttttttt    60
tt                                                                  62

<210> SEQ ID NO 59
<211> LENGTH: 61
<212> TYPE: DNA
<213> ORGANISM: Artificial Sequence
<220> FEATURE:
<223> OTHER INFORMATION: #18 Sequences on the microarray (5' to 3')

<400> SEQUENCE: 59
tcgcgggtca gcttgtgctg gatgaagtgc ctatagtgag tcgtattact gtttttttttt   60 t                                                                   61

<210> SEQ ID NO 60
<211> LENGTH: 88
<212> TYPE: DNA
<213> ORGANISM: Artificial Sequence
<220> FEATURE:
<223> OTHER INFORMATION: #19 Sequences on the microarray (5' to 3')

```
<400> SEQUENCE: 60
ggaggcgatg gcgtgctcgg tcaggtgcca cttctggttc ttggcgtcgc tgcggtccta    60
tagtgagtcg tattactgtt ttttttt                                        88

<210> SEQ ID NO 61
<211> LENGTH: 48
<212> TYPE: DNA
<213> ORGANISM: Artificial Sequence
<220> FEATURE:
<223> OTHER INFORMATION: #20 Sequences on the microarray (5' to 3')

<400> SEQUENCE: 61
tcagggcaag gcggagccta tagtgagtcg tattactgtt ttttttt                  48

<210> SEQ ID NO 62
<211> LENGTH: 62
<212> TYPE: DNA
<213> ORGANISM: Artificial Sequence
<220> FEATURE:
<223> OTHER INFORMATION: #21 Sequences on the microarray (5' to 3')

<400> SEQUENCE: 62
gcacggcctg accaaggaga tgaccatgaa cctatagtga gtcgtattac tgttttttt     60 tt                                                                   62

<210> SEQ ID NO 63
<211> LENGTH: 62
<212> TYPE: DNA
<213> ORGANISM: Artificial Sequence
<220> FEATURE:
<223> OTHER INFORMATION: #22 Sequences on the microarray (5' to 3')

<400> SEQUENCE: 63
catggagggc tgcgtggacg gccacaagtt cctatagtga gtcgtattac tgttttttt     60 tt                                                                   62

<210> SEQ ID NO 64
<211> LENGTH: 60
<212> TYPE: DNA
<213> ORGANISM: Artificial Sequence
<220> FEATURE:
<223> OTHER INFORMATION: #23 Sequences on the microarray (5' to 3')

<400> SEQUENCE: 64
cgtgatcacc ggcgagggca tcggctaccc tatagtgagt cgtattactg ttttttttt     60

<210> SEQ ID NO 65
<211> LENGTH: 62
<212> TYPE: DNA
<213> ORGANISM: Artificial Sequence
<220> FEATURE:
<223> OTHER INFORMATION: #24 Sequences on the microarray (5' to 3')

<400> SEQUENCE: 65
cttcaagggc aagcaggcca tcaacctgtg cctatagtga gtcgtattac tgttttttt     60 tt                                                                   62

<210> SEQ ID NO 66
<211> LENGTH: 61
<212> TYPE: DNA
<213> ORGANISM: Artificial Sequence
<220> FEATURE:
<223> OTHER INFORMATION: #25 Sequences on the microarray (5' to 3')
```

<400> SEQUENCE: 66
cttgcccttc gccgaggaca tcttgtccgc ctatagtgag tcgtattact gttttttttt    60
t    61

<210> SEQ ID NO 67
<211> LENGTH: 62
<212> TYPE: DNA
<213> ORGANISM: Artificial Sequence
<220> FEATURE:
<223> OTHER INFORMATION: #26 Sequences on the microarray (5' to 3')

<400> SEQUENCE: 67
caccgagtac ccccaggaca tcgtcgacta cctatagtga gtcgtattac tgttttttt    60 tt    62

<210> SEQ ID NO 68
<211> LENGTH: 61
<212> TYPE: DNA
<213> ORGANISM: Artificial Sequence
<220> FEATURE:
<223> OTHER INFORMATION: #27 Sequences on the microarray (5' to 3')

<400> SEQUENCE: 68
aactcctgcc ccgccggcta cacctgggac ctatagtgag tcgtattact gttttttttt    60
t    61

<210> SEQ ID NO 69
<211> LENGTH: 62
<212> TYPE: DNA
<213> ORGANISM: Artificial Sequence
<220> FEATURE:
<223> OTHER INFORMATION: #28 Sequences on the microarray (5' to 3')

<400> SEQUENCE: 69
ctccttcctg ttcgaggacg gcgccgtgtg cctatagtga gtcgtattac tgttttttt    60 tt    62

<210> SEQ ID NO 70
<211> LENGTH: 62
<212> TYPE: DNA
<213> ORGANISM: Artificial Sequence
<220> FEATURE:
<223> OTHER INFORMATION: #29 Sequences on the microarray (5' to 3')

<400> SEQUENCE: 70
catcaccgtg agcgtggagg agaactgcat cctatagtga gtcgtattac tgttttttt    60 tt    62

<210> SEQ ID NO 71
<211> LENGTH: 60
<212> TYPE: DNA
<213> ORGANISM: Artificial Sequence
<220> FEATURE:
<223> OTHER INFORMATION: #30 Sequences on the microarray (5' to 3')

<400> SEQUENCE: 71
gagtccaagt tctacggcgt gaacttcccc tatagtgagt cgtattactg tttttttttt    60

<210> SEQ ID NO 72
<211> LENGTH: 62
<212> TYPE: DNA

-continued

```
<213> ORGANISM: Artificial Sequence
<220> FEATURE:
<223> OTHER INFORMATION: #31 Sequences on the microarray (5' to 3')

<400> SEQUENCE: 72
agatgaccga caactgggag ccctcctgcg cctatagtga gtcgtattac tgtttttttt    60
tt                                                                  62

<210> SEQ ID NO 73
<211> LENGTH: 62
<212> TYPE: DNA
<213> ORGANISM: Artificial Sequence
<220> FEATURE:
<223> OTHER INFORMATION: #32 Sequences on the microarray (5' to 3')

<400> SEQUENCE: 73
ccccgtgccc aagcagggca tcttgaaggg cctatagtga gtcgtattac tgtttttttt    60
tt                                                                  62

<210> SEQ ID NO 74
<211> LENGTH: 62
<212> TYPE: DNA
<213> ORGANISM: Artificial Sequence
<220> FEATURE:
<223> OTHER INFORMATION: #33 Sequences on the microarray (5' to 3')

<400> SEQUENCE: 74
gtacctgctg ctgaaggacg gtggccgctt cctatagtga gtcgtattac tgtttttttt    60
tt                                                                  62

<210> SEQ ID NO 75
<211> LENGTH: 60
<212> TYPE: DNA
<213> ORGANISM: Artificial Sequence
<220> FEATURE:
<223> OTHER INFORMATION: #34 Sequences on the microarray (5' to 3')

<400> SEQUENCE: 75
cgacaccgtg tacaaggcca agtccgtgcc tatagtgagt cgtattactg tttttttttt    60

<210> SEQ ID NO 76
<211> LENGTH: 61
<212> TYPE: DNA
<213> ORGANISM: Artificial Sequence
<220> FEATURE:
<223> OTHER INFORMATION: #35 Sequences on the microarray (5' to 3')

<400> SEQUENCE: 76
gcaagatgcc cgactggcac ttcatccagc ctatagtgag tcgtattact gttttttttt    60
t                                                                   61

<210> SEQ ID NO 77
<211> LENGTH: 61
<212> TYPE: DNA
<213> ORGANISM: Artificial Sequence
<220> FEATURE:
<223> OTHER INFORMATION: #36 Sequences on the microarray (5' to 3')

<400> SEQUENCE: 77
caagctgacc cgcgaggacc gcagcgacgc ctatagtgag tcgtattact gttttttttt    60
t                                                                   61
```

```
<210> SEQ ID NO 78
<211> LENGTH: 60
<212> TYPE: DNA
<213> ORGANISM: Artificial Sequence
<220> FEATURE:
<223> OTHER INFORMATION: #37 Sequences on the microarray (5' to 3')

<400> SEQUENCE: 78
cacgccatcg cctccggctc cgccttgccc tatagtgagt cgtattactg tttttttttt    60

<210> SEQ ID NO 79
<211> LENGTH: 10
<212> TYPE: DNA
<213> ORGANISM: Artificial Sequence
<220> FEATURE:
<223> OTHER INFORMATION: Kozak consensus sequence

<400> SEQUENCE: 79
ggtcgccacc                                                           10

<210> SEQ ID NO 80
<211> LENGTH: 22
<212> TYPE: DNA
<213> ORGANISM: Artificial Sequence
<220> FEATURE:
<223> OTHER INFORMATION: T7 RNAP promoter complement

<400> SEQUENCE: 80
gtcattatgc tgagtgatat cc                                             22

<210> SEQ ID NO 81
<211> LENGTH: 22
<212> TYPE: DNA
<213> ORGANISM: Artificial Sequence
<220> FEATURE:
<223> OTHER INFORMATION: T7 RNAP promoter in solution

<400> SEQUENCE: 81
cagtaatacg actcactata gg                                             22

<210> SEQ ID NO 82
<211> LENGTH: 714
<212> TYPE: DNA
<213> ORGANISM: Artificial Sequence
<220> FEATURE:
<223> OTHER INFORMATION: ZsGreen1 target sequence

<400> SEQUENCE: 82
atggcccagt ccaagcacgg cctgaccaag gagatgacca tgaagtaccg catggagggc    60
tgcgtggacg gccacaagtt cgtgatcacc ggcgagggca tcggctaccc cttcaagggc   120
aagcaggcca tcaacctgtg cgtggtggag ggcggcccct gcccttcgc cgaggacatc    180 ttgtccgccg ccttcatgta cggcaaccgc gtgttcaccg agtaccccca ggacatcgtc   240
gactacttca agaactcctg ccccgccggc tacacctggg accgctcctt cctgttcgag   300
gacggcgccg tgtgcatctg caacgccgac atcaccgtga gcgtggagga gaactgcatg   360
taccacgagt ccaagttcta cggcgtgaac ttccccgccg acggcccecgt gatgaagaag   420 atgaccgaca actgggagcc ctcctgcgag aagatcatcc ccgtgccaa gcagggcatc    480 ttgaagggcg acgtgagcat gtacctgctg ctgaaggacg gtggccgctt gcgctgccag   540
```

-continued

```
ttcgacaccg tgtacaaggc caagtccgtg ccccgcaaga tgcccgactg gcacttcatc    600
cagcacaagc tgacccgcga ggaccgcagc gacgccaaga accagaagtg gcacctgacc    660
gagcacgcca tcgcctccgg ctccgccttg ccccatcatc accatcacca ctag          714
```